(12) United States Patent
Rademacher et al.

(10) Patent No.: US 9,352,026 B2
(45) Date of Patent: May 31, 2016

(54) NANOPARTICLE-INSULIN AND INSULIN ANALOGUE COMPOSITIONS

(71) Applicant: Midatech Limited, Abingdon (GB)

(72) Inventors: Thomas Rademacher, Oxfordshire (GB); Phillip Williams, Oxfordshire (GB)

(73) Assignee: Midatech Limited, Abingdon, Oxfordshire (GB)

( * ) Notice: Subject to any disclaimer, the term of this patent is extended or adjusted under 35 U.S.C. 154(b) by 0 days.

(21) Appl. No.: 14/608,343

(22) Filed: Jan. 29, 2015

(65) Prior Publication Data

US 2015/0216942 A1 Aug. 6, 2015

(30) Foreign Application Priority Data

Jan. 31, 2014 (GB) .................................. 1401706.5

(51) Int. Cl.
*A61K 9/14* (2006.01)
*A61K 38/28* (2006.01)
*A61K 47/26* (2006.01)
*A61K 47/48* (2006.01)
(Continued)

(52) U.S. Cl.
CPC . *A61K 38/28* (2013.01); *A61J 1/00* (2013.01); *A61K 9/143* (2013.01); *A61K 9/146* (2013.01); *A61K 47/26* (2013.01); *A61K 47/48861* (2013.01); *A61K 47/48884* (2013.01); *B65D 25/205* (2013.01)

(58) Field of Classification Search
None
See application file for complete search history.

(56) References Cited

U.S. PATENT DOCUMENTS

| 6,126,637 | A | * | 10/2000 | Kriesel | A61M 5/152 604/132 |
| 2009/0137455 | A1 | * | 5/2009 | Steiner | A61K 9/0014 514/1.1 |
| 2012/0009260 | A1 | * | 1/2012 | Schobel | A61K 9/0056 424/484 |

(Continued)

FOREIGN PATENT DOCUMENTS

| EP | 2 305 310 A1 | 4/2011 |
| WO | 0232404 A2 | 10/2001 |

(Continued)

OTHER PUBLICATIONS

Rice, Peter et al., "EMBOSS: The European Molecular Biology Open Software Suite", Trends in Genetics, 16(6): 276-77 (2000).

(Continued)

*Primary Examiner* — Jeffrey E Russel
(74) *Attorney, Agent, or Firm* — Patrick J. Hagan; Dann, Dorfman, Herrell and Skillman, P.C.

(57) ABSTRACT

The present invention relates to insulin- and insulin analog-carrying nanoparticles formulated together with or for use with free insulin or with an insulin analog, such as a rapidly-acting insulin analog. The compositions of the present invention find use in medicine, particularly in glycemic control, e.g. for controlling blood glucose levels in diabetic subjects. Nanoparticle compositions of the invention, formulated together with or for use with free insulin or with an insulin analog, comprise a nanoparticle comprising a core comprising a metal and/or a semiconductor; and a corona comprising a plurality of ligands covalently linked to the core, wherein said plurality of ligands comprise at least one carbohydrate moiety; and at least one insulin peptide and/or insulin analog peptide that is non-covalently bound to the corona.

19 Claims, 14 Drawing Sheets

(51) Int. Cl.
   *A61J 1/00* (2006.01)
   *B65D 25/20* (2006.01)

(56) References Cited

U.S. PATENT DOCUMENTS

| | | | | |
|---|---|---|---|---|
| 2012/0035103 | A1* | 2/2012 | Pillion | A61K 38/28 514/6.3 |
| 2012/0171291 | A1* | 7/2012 | Rademacher | A61K 47/48861 424/490 |
| 2012/0295846 | A1* | 11/2012 | Hagendorf | A61K 9/0019 514/6.5 |

FOREIGN PATENT DOCUMENTS

| | | |
|---|---|---|
| WO | 2004108165 A2 | 6/2004 |
| WO | 2005091704 A2 | 3/2005 |
| WO | 2005116226 A2 | 5/2005 |
| WO | 2006037979 A2 | 9/2005 |
| WO | 2007015105 A2 | 8/2006 |
| WO | 2007122388 A2 | 4/2007 |
| WO | 2011/156711 A1 | 12/2011 |
| WO | 2011154711 A1 | 12/2011 |
| WO | 2012/170828 A1 | 12/2012 |

OTHER PUBLICATIONS

Cao, Y.C. et al., "Nanoparticles with Raman Spectroscopic Fingerprints for DNA and RNA Detection", Science, 297:1536-1539 (2002).

Vestal, Christy R. et al., "Effects of Surface Coordination Chemistry on the Magnetic Properties of MnFe2O4 Spinel Ferrite Nanoparticles", J. Am. Chem. Soc., 125: 9828-33 (2003).

Neveu, S. et al., "Size-Selective Chemical Synthesis of Tartrate Stabilized Cobalt Ferrite Ionic Magnetic Fluid", J. Colloid Interface Sci., 255: 293-298 (2002).

Huang, Shih-Hung et al., "Direct Binding and Characterization of Lipase onto Magnetic Nanoparticles", Biotechnol. Prog., 19: 1095-1100 (2003).

Barrientos, Africa G., "Transbuccal Insulin-Glyconanoparticles: An Alternative to Injectable Insulin", retrieved from the Internet, URL:http://www.egsf.org/assets/meeting-report.pdf, Oral Communication OC-16, Jul. 2012 [Abstract only].

Bhumkar, Devika R. et al., "Chitosan Reduced Gold Nanoparticles as Novel Carriers for Transmucosal Delivery of Insulin", Pharmaceutical Research, 24(8): 1415-1426 (2007).

International Search Report/Written Opinion issued Apr. 28, 2015 in related International Application No. PCT/GB2015/050210, filed Jan. 29, 2015.

* cited by examiner

NANOPARTICLE-INSULIN AND INSULIN ANALOGUE COMPOSITIONS

FIELD OF THE INVENTION

The present invention relates to peptide-carrying nanoparticles, particularly for use in medicine, and includes methods for treatment of disorders, e.g., of diabetes.

BACKGROUND TO THE INVENTION

The present invention is directed at compositions and products, and methods of making and administering such compositions and products, including for the treatment of mammals and particularly humans.

Bioactive agents, such as peptides, frequently suffer from poor stability, particularly thermo-stability, which may limit the conditions to which the agents can be subjected during preparation, processing, storage and/or delivery. Medical preparations of peptides for human use are generally formulated with one or more preservatives and/or stabilisers. Moreover, limited gastrointestinal stability typically presents a barrier to effective oral administration of bioactive peptides. WO 2011/154711 describes glyconanoparticles that have a gold core surrounded by a carbohydrate corona and which act as carriers for peptides such as insulin.

Fast-acting analogues of insulin include insulin lispro (Humalog®, Eli Lilly and Company), insulin aspart (NovoRapid®, Novo Nordisk A/S) and insulin glulisine (Apidra®, Sanofi-Aventis). Fast-acting insulin analogues are typically administered as meal time insulin for post-prandial glucose control in diabetic patients. Compared with regular insulin, these analogue exhibit a shortened delay of onset, allowing more flexibility in the coordination of meal times and insulin administration.

There remains an unmet need for further bioactive peptide compositions, in particular for delivery of insulin and rapid-acting analogues thereof. There remains an unmet need for pharmaceutical compositions and/or formulations of rapid acting insulin analogues which restore the neural counter-hormone response of such analogues and thereby reduce the incidence of hypoglycemia.

The present invention addresses these and other needs.

BRIEF DESCRIPTION OF THE INVENTION

Broadly, the present invention relates to formulations of insulin-carrying nanoparticles, including co-formulations of one or more rapid-acting insulin analogues with insulin analogue-carrying nanoparticles. The present inventors have found that nanoparticle-carried fast-acting insulin analogues exhibit a hormetic-type response comparable to normal free insulin, a response that is largely lacking from the same fast-acting insulin analogues when administered as free peptides. The restoration of the "lost" neural counter-hormone response is both advantageous and unexpected. It is presently believed, based on the data described herein, that the inclusion of nanoparticle-carried fast-acting insulin analogue in a pharmaceutical formulation of the fast-acting insulin analogue will reduce the likelihood or incidence of unwanted hypoglycemic events, e.g. among insulin-dependent diabetic subjects.

Accordingly, in a first aspect the present invention provides a pharmaceutical composition comprising:
(i) free insulin or a free peptide analogue thereof; and
(ii) a plurality of nanoparticles, each of said nanoparticles comprising:
    (a) a core comprising a metal and/or a semiconductor;
    (b) a corona comprising a plurality of ligands covalently linked to the core, wherein at least one of said ligands comprises a carbohydrate moiety; and
    (c) at least one insulin molecule or peptide analogue thereof non-covalently bound to the corona,
wherein the molar ratio of free insulin or free peptide analogue thereof to the nanoparticle-bound insulin or nanoparticle-bound peptide analogue thereof is in the range 1:1 to 100:1.

In some cases in accordance with this and other aspects of the present invention, the peptide analogue of insulin has at least 70%, 80%, 90%, 95% or at least 99% amino acid sequence identity to the human insulin sequence of SEQ ID NO: 1 and is of between 40 and 60 amino acids in length.

In some cases in accordance with this and other aspects of the present invention, the peptide analogue of insulin is selected from the group consisting of: insulin glulisine; insulin aspart; insulin lispro; NPH insulin; insulin glargine; insulin detemir; and insulin degludec.

In some cases in accordance with this and other aspects of the present invention, the peptide analogue of insulin exhibits a central nervous system uptake in a mammalian subject that is 50%, 20%, 10%, 5% or less of the a central nervous system uptake of native human insulin having the amino acid sequence of SEQ ID NO: 1.

In some cases in accordance with this and other aspects of the present invention, the peptide analogue of insulin is an insulin analogue that induces at least transient hypoglycemia when administered to a mammalian subject as a free peptide composition in the absence of nanoparticle-bound insulin or nanoparticle-bound insulin analogue.

In some cases in accordance with this and other aspects of the present invention, the nanoparticle-bound insulin or nanoparticle-bound insulin analogue induces an increase in plasma adrenalin concentration and/or plasma growth hormone concentration upon administration to a mammalian subject.

In a second aspect, the present invention provides a method of regulating blood glucose concentration in a diabetic or pre-diabetic mammalian subject, said method comprising administering to the subject an effective amount of the pharmaceutical composition in accordance with the first aspect of the invention.

In a third aspect, the present invention provides a method of reducing the incidence of hypoglycemic adverse events in an insulin-dependent diabetic or pre-diabetic mammalian subject, said method comprising:
administering, simultaneously, sequentially or concurrently with a dose of insulin or a peptide analogue thereof, an effective amount of the pharmaceutical composition comprising a plurality of nanoparticles, each of said nanoparticles comprising:
    (a) a core comprising a metal and/or a semiconductor;
    (b) a corona comprising a plurality of ligands covalently linked to the core, wherein at least one of said ligands comprises a carbohydrate moiety; and
    (c) at least one insulin molecule or peptide analogue thereof non-covalently bound to the corona. When administration is sequential the dose of free insulin or peptide analogue thereof and the dose of nanoparticle-bound insulin or analogue thereof may be administered in any order. Moreover, when administration is sequential the dose of free insulin or peptide analogue thereof and the dose of nanoparticle-bound insulin or analogue thereof may, in some cases, be administered between 1 second and 1 hour apart, e.g.

between 1 minute and 10 minutes apart, or between 2 minutes and 5 minutes apart.

In a fourth aspect, the present invention provides a pharmaceutical composition in accordance with the first aspect of the invention for use in medicine.

In a fifth aspect, the present invention provides a pharmaceutical composition in accordance with the first aspect of the invention for use in a method in accordance with the second or third aspects of the present invention.

In a sixth aspect, the present invention provides use of a pharmaceutical composition in accordance with the first aspect of the invention for use in the preparation of a medicament for use in a therapeutic method in accordance with the second or third aspects of the present invention.

In accordance with any one of the aspects of the present invention, the corona may comprise one or more carbohydrate ligands, for example one or more monosaccharide ligands, covalently attached to the core via a linker.

In accordance with any one of the aspects of the present invention, the insulin or analogue thereof may comprise or consist of an amino acid A chain having at least 70%, 80%, 90%, 95% or 99% amino acid sequence identity with the full-length amino acid sequence set forth as SEQ ID NO: 1 and an amino acid B chain having at least 70%, 80%, 90%, 95% or 99% amino acid sequence identity with any one of the full-length amino acid sequences set forth as SEQ ID NOS: 2-5, wherein the A and B chains are linked. In some cases, the link between the A and B chains comprises at least one or at least two disulphide bonds. In some cases, the analogue of insulin comprises an A chain that has up to 1, 2, 3, 4 or 5 amino acid changes by substitution, addition and/or deletion as compared with the full-length A chain amino acid sequence set forth in SEQ ID NO: 1. In some cases, the analogue of insulin comprises a B chain that has up to 1, 2, 3, 4 or 5 amino acid changes by substitution, addition and/or deletion as compared with any one of the full-length B chain amino acid sequences set forth in SEQ ID NOS: 2-5.

The human insulin sequence is disclosed at UniProt accession no. P01308, version 186, dated 13 Nov. 2013. Human insulin is a heterodimer of insulin A chain and insulin B chain linked by two disulphide bonds.

The A chain (consisting of residues 90-110 of the 110 amino acid sequence of preproinsulin) has the following sequence:
>sp|P01308|90-110
GIVEQCCTSICSLYQLENYCN (SEQ ID NO: 1)

The B chain (consisting of residues 25-54 of the 110 amino acid sequence of preproinsulin) has the following sequence:
>sp|P01308|25-54
FVNQHLCGSHLVEALYLVCGERGFFYTPKT (SEQ ID NO: 2)

The A and B chains are linked by two disulphide bonds: a first interchain bond between Cys31 of the B chain and Cys 96 of the A chain (numbered according to the preproinsulin sequence) and a second interchain bond between Cys43 of the B chain and Cys109 of the A chain (numbered according to the preproinsulin sequence).

In some cases in accordance with any aspect of the present invention, the analogue of insulin may be a fast-acting insulin analogue. In particular, the insulin analogue may be selected from the group consisting of: insulin lispro (Humalog®, Eli Lilly and Company), insulin aspart (NovoRapid®, Novo Nordisk A/S) and insulin glulisine (Apidra®, Sanofi-Aventis).

Insulin lispro is a fast-acting insulin analogue having an inversion of Lys28 and Pro29 of the B chain compared with native insulin (i.e. positions 52 and 53 numbered according to the preproinsulin sequence). The B chain of insulin lispro therefore has the amino acid sequence FVNQHLCGSHLVEALYLVCGERGFFYT<u>KP</u>T (SEQ ID NO: 3).

Insulin aspart is a fast-acting insulin analogue having the amino acid substitution Pro28Asp in the B chain compared with native insulin (i.e. position 52 numbered according to the preproinsulin sequence). The B chain of insulin aspart therefore has the amino acid sequence FVNQHLCGSHLVEALYLVCGERGFFYT<u>D</u>KT (SEQ ID NO: 4).

Insulin glulisine is a fast-acting insulin analogue having the amino acid substitutions Asn3Lys and Lys29Glu in the B chain compared with native insulin (i.e. positions 27 and 53 numbered according to the preproinsulin sequence). The B chain of insulin glulisine therefore has the amino acid sequence FV<u>K</u>QHLCGSHLVEALYLVCGERGFFYTP<u>E</u>T (SEQ ID NO: 5).

It has been found that the nanoparticles in accordance with the present invention may be provided with a variety of numbers of ligands forming the corona. For example, in some cases the corona comprises at least 5, 10, 20 or at least 50 ligands per core, e.g. between about 10 to about 1000 ligands per core. In particular, the nanoparticle compositions in accordance with any aspect of the present invention may comprise at least 5, 10, 15, 20 or at least 50 glutathione ligands and/or carbohydrate ligands per core.

The number of insulin peptide molecules and/or insulin analogue peptide molecules bound per core is not particularly limited. For certain applications, it may be desirable to employ as few as 1, 2, 3 or 4 insulin peptides and/or insulin analogue peptides per core, while in other cases the nanoparticle of the invention may comprise at least 5, 10, 15, 20, 30 or at least 50 or more insulin peptides and/or insulin analogue peptides bound per core. In some cases the nanoparticle of the invention may comprise between 10 and 30 (e.g. approximately 20) glulisine peptide molecules per nanoparticle core.

In some cases, in accordance with any one of the aspects of the present invention, the at least one insulin peptide and/or insulin analogue peptide may be bound to the corona of the nanoparticle in a reversible manner. In particular, the insulin peptide and/or insulin analogue peptide may be bound to the corona such that at least a fraction of the bound peptide is released from the nanoparticle upon contacting the nanoparticle with a physiological solution. The insulin peptide and/or insulin analogue peptide may in some cases be adsorbed to the corona of the nanoparticle. The insulin peptide and/or insulin analogue peptide may in some cases be electrostatically or otherwise non-covalently bound to the one or more ligands that form the corona of the nanoparticle.

In some cases, in accordance with any one of the aspects of the present invention, said ligands comprise a carbohydrate-containing ligands alone or in conjunction with other species of ligand, e.g., combinations of carbohydrate ligands (including, e.g., alpha-galactose-containing ligands) and non-carbohydrate containing ligands are specifically contemplated herein. The one or more species of ligand may be selected from one or more of the ligands that form the corona of the nanoparticles disclosed in WO2011/154711, the entire contents of which is expressly incorporated herein by reference.

In some cases in accordance with any one of the aspects of the present invention said carbohydrate moiety may comprises a monosaccharide and/or a disaccharide. The carbohydrate moiety may be as defined further herein, including a carbohydrate mimetic. The carbohydrate moiety may be covalently linked to the core via a linker selected from the group consisting of: sulphur-containing linkers, amino-containing linkers, phosphate-containing linkers and oxygen-containing linkers. In some cases the linker comprises an alkyl chain of at least two carbons. In some cases the carbohydrate-containing ligand or ligands may be other than chitosan.

In accordance with the present invention said at least one ligand comprising a carbohydrate moiety may in some cases be selected from the group consisting of: 2'-thioethyl-α-D-galactopyranoside, 2'-thioethyl-β-D-glucopyranoside, 2'-thioethyl-2-acetamido-2-deoxy-β-D-glucopyranoside, 5'-thiopentanyl-2-deoxy-2-imidazolacetamido-α,β-D-glucopyranoside and 2'-thioethyl-α-D-glucopyranoside, wherein said at least one ligand comprising a carbohydrate moiety is covalently linked to the core via its sulphur atom.

It is specifically contemplated herein that said plurality of ligands covalently linked to the core may comprise at least a first ligand and a second ligand, wherein the first and second ligands are different. For example the first and second ligands may be as follows:
  (a) said first ligand comprises 2'-thioethyl-α-D-galactopyranoside and said second ligand comprises 1-amino-17-mercapto-3,6,9,12,15,-pentaoxa-heptadecanol;
  (b) said first ligand comprises 2'-thioethyl-β-D-glucopyranoside or 2'-thioethyl-α-D-glucopyranoside and said second ligand comprises 5'-thiopentanyl-2-deoxy-2-imidazolacetamido-α,β-D-glucopyranoside;
  (c) said first ligand comprises 2'-thioethyl-β-D-glucopyranoside or 2'-thioethyl-α-D-glucopyranoside and said second ligand comprises 1-amino-17-mercapto-3,6,9,12,15,-pentaoxa-heptadecanol; or
  (d) said first ligand comprises 2'-thioethyl-2-acetamido-2-deoxy-β-D-glucopyranoside and said second ligand comprises 1-amino-17-mercapto-3,6,9,12,15,-pentaoxa-heptadecanol,
and wherein said first and second ligands are covalently linked to the core via their respective sulphur atoms.

In some cases the first ligand may comprise a carbohydrate moiety and said second ligand a non-carbohydrate ligand. One or more of the ligands may an amine group. In particular, the second ligand may comprise 1-amino-17-mercapto-3,6,9,12,15,-pentaoxa-heptadecanol covalently linked to the core via its sulphur atom.

As described further herein, where there different ligands are present on the nanoparticle they may be present at, e.g., certain defined ratios or ranges of ratios. For example, the first ligand and said second ligand may present on the nanoparticle in a molar ratio in the range of 1:40 to 40:1, 1:10 to 10:1 or even 1:2 to 2:1.

In accordance with the present invention the nanoparticle of the invention may comprise a component having a divalent state, such as a metal or a compound having a divalent state, or an oxide or salt thereof. For example, metals or metal complexes having the ability to exist in a divalent state are particularly useful. Such a component may be in the divalent state as added or may be transformed into a divalent state after addition. Oxides and salts of the divalent component are also useful and may be added directly or formed in situ subsequent to addition. Among the useful salts of the divalent component include halide salts, such as chloride, iodide, bromide and fluoride. Such divalent components may include, for example, zinc, magnesium, copper, nickel, cobalt, cadmium, or calcium, and their oxides and salts thereof. The component is desirably present in an amount sufficient to produce a stabilizing effect and/or in an amount sufficient to enhance the binding of the peptide to the corona to a level greater than the level of binding of the peptide to the corona in the absence of the component having a divalent state. In some cases, the component having a divalent state is desirably present in an amount of about 0.5 to 2.0 equivalents to the core metal (e.g. gold), or optionally about 0.75 to 1.5 equivalents to the core metal (e.g. gold). In the context of the present invention, "equivalents" may be mole equivalents, for example 1.0 equivalent of zinc may be taken to mean the same number of zinc atoms or $Zn^{2+}$ cations as the number of gold atoms in the core of the nanoparticle.

The divalent component may in some cases be present in the corona of the nanoparticle. It is specifically contemplated herein that the divalent component may be included in the nanoparticle, including in the corona of the nanoparticle as a result of inclusion of the divalent component in the process of synthesis of the nanoparticle. Additionally or alternatively, the divalent component may be added after synthesis of the nanoparticle. In some cases in accordance with the present invention, the divalent component, such as zinc may be selected from: $Zn^{2+}$ and ZnO. For example, the zinc may be in the form of $ZnCl_2$.

In some cases, in accordance with any one of the aspects of the present invention, the diameter of the core of the nanoparticle is in the range 1 nm to 5 nm.

In some cases, in accordance with any one of the aspects of the present invention, the diameter of the nanoparticle including its ligands is in the range 2 nm to 50 nm, optionally 3 nm to 30 nm, or 4 nm to 20 nm, or 5 nm to 15 nm.

In some cases, in accordance with any one of the aspects of the present invention, the core comprises a metal selected from the group consisting of: Au, Ag, Cu, Pt, Pd, Fe, Co, Gd and Zn, or any combination thereof.

In some cases, in accordance with any one of the aspects of the present invention, the core is magnetic.

In some cases, in accordance with any one of the aspects of the present invention, the core comprises a semiconductor. The semiconductor may comprise metal atoms, such as cadmium. Alternatively or additionally, the semiconductor may comprise non-metal atoms. Organic semiconductors are specifically contemplated herein. Preferred semiconductors, in accordance with the present invention, may be selected from the group consisting of: cadmium selenide, cadmium sulphide, cadmium tellurium and zinc sulphide.

In some cases, in accordance with any one of the aspects of the present invention, the core is capable of acting as a quantum dot.

Preferably, the composition in accordance with the first aspect of the invention comprises a plurality, e.g., 100, 1000, 100000, or more, of said nanoparticles, wherein at least 10%, 20%, 30%, 40%, 50%, 60%, 70%, 80%, 90% or 95% of the nanoparticles in said composition have at least one insulin or insulin analogue peptide bound.

In some cases, in accordance with any one of the aspects of the present invention, the plurality of nanoparticles are formulated in a carrier, such as solution, a polymer (e.g. a viscoelastic polymer film), a powder, or a cream, in which the nanoparticles and bound insulin and/or insulin analogue peptides are suspended and/or embedded. In certain cases, the nanoparticle formulation may be in the form of a patch or film for delivery to or across skin, mouth, cheek (transbuccal), vagina, rectum or in the form of a spray for delivery into the mouth, nose, lungs or the rectum or vagina. The formulation may be in an associated form, a suspension or contained together in a single package, container or carrier (e.g. wherein both the plurality of nanoparticles and the free peptide insulin or free peptide insulin analogue are in a single package, container or carrier).

In certain cases, the pharmaceutical composition in accordance with any one of the aspects of the present invention may take the form of one or more doses (e.g. a defined quantity of insulin peptide or analogue thereof, or insulin peptide activity units), such as in the form of a therapeutic dose or defined number of doses. In certain cases the nanoparticle portion of the pharmaceutical composition may be in the form of a viscoelastic polymer film for transbuccal delivery.

In some cases, in accordance with any one of the aspects of the present invention, the plurality of nanoparticles may further comprise at least one permeation enhancer that is non-covalently or covalently bound to said core and/or or said corona. As described in co-pending GB patent application No. 1301991.4, filed 5 Feb. 2013, the entire contents of which are expressly incorporated herein by reference for all purposes, certain permeation enhancers may be advantageously bound to the nanoparticle without displacing any significant active peptide, such as the insulin peptide or analogue thereof as defined herein. In certain cases, said permeation enhancer is selected from tetradecyl-D-maltoside and lysalbinic acid. In certain cases, said permeation enhancer, e.g. tetradecyl-D-maltoside and/or lysalbinic acid is non-covalently bound to said corona.

In accordance with any one of the second to sixth aspects of the invention, the subject may be a human, a companion animal (e.g. a dog or cat), a laboratory animal (e.g. a mouse, rat, rabbit, pig or non-human primate), a domestic or farm animal (e.g. a pig, cow, horse or sheep). Preferably, the subject is a human. In some cases the subject has type 1 diabetes, type 2 diabetes or prediabetes.

In accordance with any one of the second to sixth aspects of the invention, the subject may in certain cases have a disorder that results in abnormally lowered blood glucose concentration (i.e. hypoglycemia). Hypoglycemia may be a temporary state resulting from poor management of a diabetic condition, for example where too much insulin has been administered or insufficient food taken in or the insulin and food intake have been poorly timed such that the subject enters a state of hypoglycemia. Without wishing to be bound by any particular theory, the present inventors believe that the comparative paucity of neural recognition of rapidly-acting insulin analogues when delivered in conventional formulations may result in unwanted hypoglycemia (e.g. hypoglycemia may result if a rapidly-acting insulin analogue is administered and the subject does not then eat within around 15 minutes). However, as described in the examples herein, insulin or analogues thereof (including rapidly-acting analogues) delivered bound to nanoparticles as defined herein are believed to exhibit superior neural recognition in a mammalian subject as compared with rapidly-acting insulin analogues delivered in conventional formulations (e.g. via subcutaneous injection of free peptide formulations). Therefore, nanoparticle-bound insulin and/or insulin analogue peptide may be advantageously administered with a rapidly-acting insulin analogue at or around the time that the rapidly-acting insulin analogue is administered in a conventional formulation (e.g. via subcutaneous injection of free peptide formulations) and thereby reducing or avoiding hypoglycemia induced by the free rapidly-acting insulin analogue peptide.

In accordance with any one of the second to sixth aspects of the invention, it is specifically contemplated that, in some cases, the composition of the invention may be self-administered or for self-administration.

In accordance with any one of the second to sixth aspects of the invention, the plurality of nanoparticles may be administered or for administration with (i.e. simultaneously, separately or sequentially) one or more therapeutic agents for the control of diabetes.

In accordance with any one of the second to sixth aspects of the invention, the plurality of nanoparticles may be administered or for administration by any suitable route. In particular cases, the plurality of nanoparticles may be administered or for administration via a route selected from the group consisting of: intravenous (i.v.), intramuscular (i.m.), intradermal (i.d.), intraperitoneal or subcutaneous (s.c.) injection or infusion; buccal; sublabial; sublingual; by inhalation; via one or more mucosal membranes; urogenital; rectal; intranasal and dermal.

In a seventh aspect, the present invention provides an article of manufacture comprising:
   a pharmaceutical composition as defined in accordance with the first aspect of the invention;
   a container for housing the pharmaceutical composition; and
   an insert and/or label. Preferably, the insert and/or label provide instructions, dosage and/or administration information relating to the use of the pharmaceutical composition in a method of managing blood glucose concentration (glycemic control) and/or a method of managing or treating diabetes.

In an eighth aspect, the present invention provides a process for producing a pharmaceutical composition as defined in accordance with the first aspect of the invention, the process comprising:
   providing a nanoparticle comprising a core comprising a metal and/or a semiconductor and a corona comprising a plurality of ligands covalently linked to the core, wherein said ligands comprise one or more carbohydrate-containing ligands (e.g. galactose-containing ligands);
   contacting the nanoparticle with at least one insulin peptide and/or insulin analogue peptide as defined herein under conditions which allow the at least one insulin peptide and/or insulin analogue peptide to bind to the corona of the nanoparticle; and
   combining the resulting nanoparticle having insulin peptide and/or insulin analogue peptide bound thereto with insulin peptide and/or insulin analogue peptide that is not bound to a nanoparticle.

In some cases in accordance with this aspect of the present invention, said combining step comprises including the nanoparticle having insulin peptide and/or insulin analogue peptide bound thereto in a housing or container with the insulin peptide and/or insulin analogue peptide that is not bound to a nanoparticle. The insulin analogue peptide may be a rapidly-acting insulin analogue as further defined herein.

In some cases, in accordance with this aspect of the present invention, the process comprises an earlier step of producing the nanoparticle, said earlier step comprising: combining a solution comprising one or more derivatised carbohydrate moieties (e.g. thioethyl-alpha galactose) with a solution comprising a core-forming material (e.g. gold III chloride) and with a reducing agent (e.g. sodium borohydride), thereby causing the nanoparticle to self-assemble.

The present invention includes the combination of the aspects and preferred features described except where such a combination is clearly impermissible or is stated to be expressly avoided. These and further aspects and embodiments of the invention are described in further detail below and with reference to the accompanying examples and figures.

BRIEF DESCRIPTION OF THE FIGURES

FIG. 2A—Control animals receiving no insulin; FIG. 2B—Test animals receiving intravenous (i.v.) nanoparticle-bound insulin; FIG. 2C—Control animals receiving 2.5 units of subcutaneous (s.c.) NovoRapid® insulin aspart; FIG. 2D—Test animals receiving transbuccal GNP-regular insulin formulated in PharmFilm™. Each of these curves can be transformed, and early (K1), and late (K2) rate constants for glucose clearance calculated. The results show hypoglycemia for s.c. NovoRapid® (see panel C), but no hypoglycemia for nanoparticle-bound insulin (see panels B and D).

FIG. 3A—An s.c. injection of 2.5 U/animal regular (Diosynth) free insulin was administered to anaesthetized minipigs (1-squares; 2-circles; 3-triangles; and 4-inverted triangles) and blood glucose concentration plotted against time. FIG. 3B—An s.c. injection of 2.5 U/animal gold nanoparticle (GNP)-bound regular (Diosynth) insulin was administered to anaesthetized minipigs (1-squares; 2-circles; 3-triangles; and 4-inverted triangles) and blood glucose concentration plotted against time. FIG. 3C—In a further experiment, an s.c. injection of 2.5 U/animal gold nanoparticle (GNP)-bound regular (Diosynth) insulin was administered to anaesthetized minipigs (1-squares; 2-circles; 3-triangles; and 4-inverted triangles) and blood glucose concentration plotted against time. The results show that in these insulin stress tests neither s.c. administration of regular insulin or GNP-I insulin results in hypoglycemia.

FIG. 5A—Adrenalin (left-hand y-axis) and glucose (right-hand y-axis) concentrations are plotted against time for 0.15 U/kg s.c. administered Apidra® in anaesthetised minipigs. FIG. 5B—Glucagon (left-hand y-axis) and glucose (right-hand y-axis) concentrations are plotted against time for 0.15 U/kg s.c. administered Apidra® in anaesthetised minipigs. FIG. 5C—Growth hormone (left-hand y-axis) and glucose (right-hand y-axis) concentrations are plotted against time for 0.15 U/kg s.c. administered Apidra® in anaesthetised minipigs. The results shown in this insulin stress test demonstrate that, despite induction of hypoglycemia, the Apidra® does not generate a counter-hormone response. S.c. administered Apidra® only induces counter-hormone release post-anesthesia; there is no induction of early hypoglycemia recognition.

FIG. 6A—Adrenalin (left-hand y-axis) and glucose (right-hand y-axis) concentrations are plotted against time for transbuccally administered, gold nanoparticle-bound Apidra® (TB-GNP-Apidra®). FIG. 6B—Growth hormone (GH) (left-hand y-axis) and glucose (right-hand y-axis) concentrations are plotted against time for transbuccally administered, gold nanoparticle-bound Apidra® (TB-GNP-Apidra®). The observed immediate rise of plasma adrenalin and GH to TB-GNP-Apidra® could explain the quick rise in blood glucose post-TB-GNP-Apidra® administration.

DETAILED DESCRIPTION OF THE INVENTION

Figure 1:
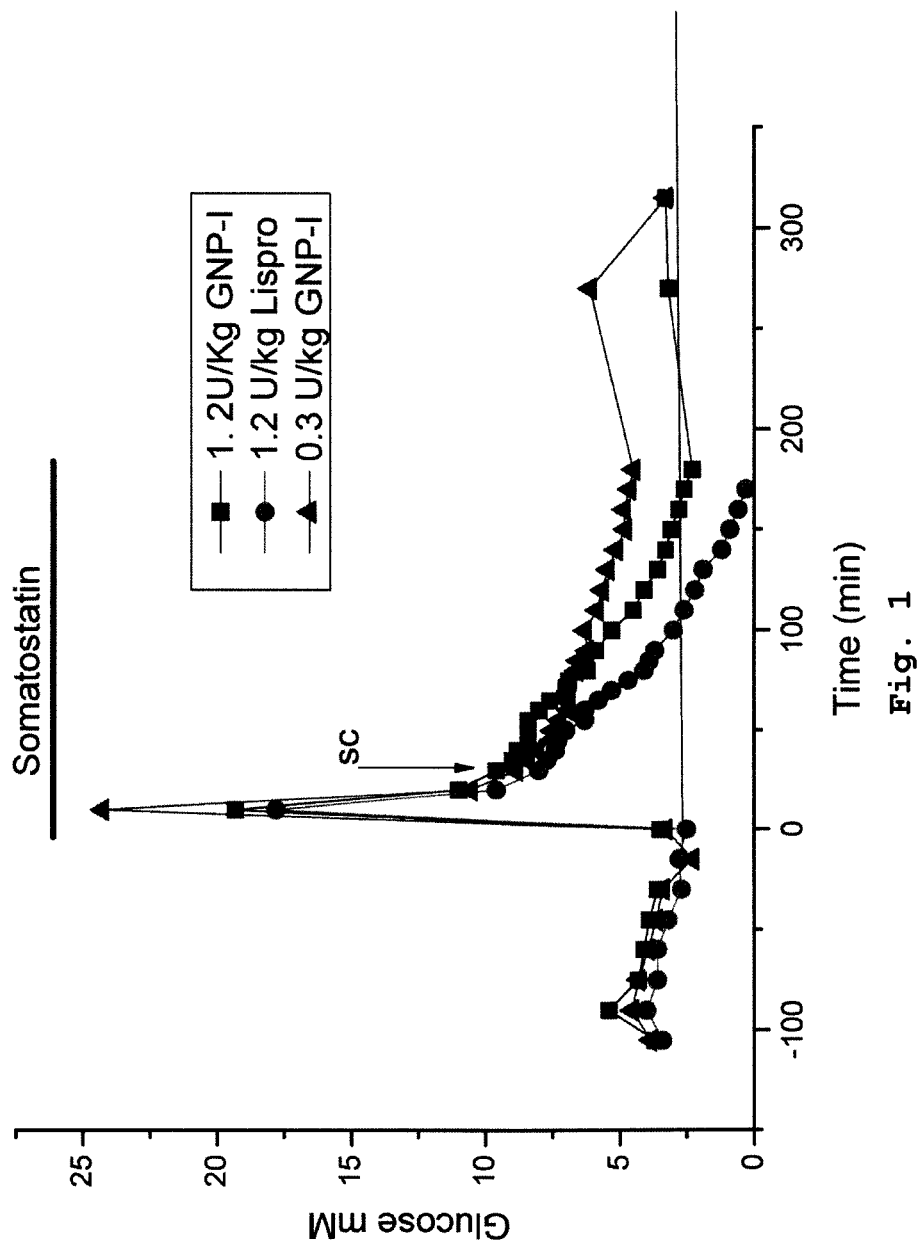
FIG. 1 shows minipig plasma glucose plotted against time for 1.2 U/kg gold nanoparticle-bound insulin ("GNP-I"; filled squares); 0.3 U/kg GNPI (filled triangles); and 1.2 U/kg free insulin lispro (filled circles). Somatostatin is indicated by the dark bar at the top of the figure. The results indicate that for equal subcutaneous (s.c.) dose of analogue insulin lispro and GNP-regular insulin the analogue insulin lispr results in hypoglycemia relative to nanoparticle-bound insulin.

In describing the present invention, the following terms will be employed, and are intended to be defined as indicated below.

As used herein, "nanoparticle" refers to a particle having a nanomeric scale, and is not intended to convey any specific shape limitation. In particular, "nanoparticle" encompasses nanospheres, nanotubes, nanoboxes, nanoclusters, nanorods and the like. In certain embodiments the nanoparticles and/or nanoparticle cores contemplated herein have a generally polyhedral or spherical geometry.

Nanoparticles comprising a plurality of carbohydrate-containing ligands have been described in, for example, WO 2002/032404, WO 2004/108165, WO 2005/116226, WO 2006/037979, WO 2007/015105, WO 2007/122388, WO 2005/091704, WO 2011/154711 (the entire contents of each of which is expressly incorporated herein by reference) and such nanoparticles may find use in accordance with the present invention. Moreover, gold-coated nanoparticles comprising a magnetic core of iron oxide ferrites (having the formula $XFe_2O_4$, where X=Fe, Mn or Co) functionalised with organic compounds (e.g. via a thiol-gold bond) are described in EP2305310 (the entire contents of which is expressly incorporated herein by reference) and are specifically contemplated for use as nanoparticles/nanoparticle cores in accordance with the present invention.

As used herein, "corona" refers to a layer or coating, which may partially or completely cover the exposed surface of the nanoparticle core. The corona includes a plurality of ligands which generally include at least one carbohydrate moiety, one surfactant moiety and/or one glutathione moiety. Thus, the corona may be considered to be an organic layer that surrounds or partially surrounds the metallic and/or semiconductor core. In certain embodiments the corona provides and/or participates in "passivating" the core of the nanoparticle. Thus, in certain cases the corona may include a sufficiently complete coating layer substantially to stabilise the semiconductor or metal-containing core. However, it is specifically contemplated herein that certain nanoparticles having cores, e.g., that include a metal oxide-containing inner core coated with a noble metal may include a corona that only partially coats the core surface. In certain cases the corona facilitates solubility, such as water solubility, of the nanoparticles of the present invention.

Nanoparticles

Nanoparticles are small particles, e.g. clusters of metal or semiconductor atoms, that can be used as a substrate for immobilising ligands.

Preferably, the nanoparticles have cores having mean diameters between 0.5 and 50 nm, more preferably between 0.5 and 10 nm, more preferably between 0.5 and 5 nm, more preferably between 0.5 and 3 nm and still more preferably between 0.5 and 2.5 nm. When the ligands are considered in addition to the cores, preferably the overall mean diameter of the particles is between 2.0 and 20 nm, more preferably between 3 and 10 nm and most preferably between 4 and 5 nm. The mean diameter can be measured using techniques well known in the art such as transmission electron microscopy.

The core material can be a metal and/or semiconductor (said semiconductor optionally comprising metal atoms or being an organic semiconductor) and may be formed of more than one type of atom. Preferably, the core material is a metal selected from Au, Fe or Cu. Nanoparticle cores may also be formed from alloys including Au/Fe, Au/Cu, Au/Gd, Au/Fe/Cu, Au/Fe/Gd and Au/Fe/Cu/Gd, and may be used in the present invention. Preferred core materials are Au and Fe, with the most preferred material being Au. The cores of the nanoparticles preferably comprise between about 100 and 500 atoms (e.g. gold atoms) to provide core diameters in the nanometer range. Other particularly useful core materials are doped with one or more atoms that are NMR active, allowing the nanoparticles to be detected using NMR, both in vitro and in vivo. Examples of NMR active atoms include $Mn^{+2}$, $Gd^{+3}$, $Eu^{+2}$, $Cu^{+2}$, $V^{+2}$, $Co^{+2}$, $Ni^{+2}$, $Fe^{+2}$, $Fe^{+3}$ and lanthanides$^{+3}$, or the quantum dots described elsewhere in this application.

Nanoparticle cores comprising semiconductor compounds can be detected as nanometer scale semiconductor crystals are capable of acting as quantum dots, that is they can absorb light thereby exciting electrons in the materials to higher energy levels, subsequently releasing photons of light at frequencies characteristic of the material. An example of a semiconductor core material is cadmium selenide, cadmium sulphide, cadmium tellurium. Also included are the zinc compounds such as zinc sulphide.

In some embodiments, the core of the nanoparticles may be magnetic and comprise magnetic metal atoms, optionally in combination with passive metal atoms. By way of example, the passive metal may be gold, platinum, silver or copper, and the magnetic metal may be iron or gadolinium. In preferred embodiments, the passive metal is gold and the magnetic metal is iron. In this case, conveniently the ratio of passive metal atoms to magnetic metal atoms in the core is between about 5:0.1 and about 2:5. More preferably, the ratio is between about 5:0.1 and about 5:1. As used herein, the term "passive metals" refers to metals which do not show magnetic properties and are chemically stable to oxidation. The passive metals may be diamagnetic or superparamagnetic. Preferably, such nanoparticles are superparamagnetic.

Examples of nanoparticles which have cores comprising a paramagnetic metal, include those comprising $Mn^{+2}$, $Gd^{+3}$, $Eu^{+2}$, $Cu^{+2}$, $V^{+2}$, $Co^{+2}$, $Ni^{+2}$, $Fe^{+2}$, $Fe^{+3}$ and lanthanides$^{+3}$.

Other magnetic nanoparticles may be formed from materials such as MnFe (spinel ferrite) or CoFe (cobalt ferrite) can be formed into nanoparticles (magnetic fluid, with or without the addition of a further core material as defined above. Examples of the self-assembly attachment chemistry for producing such nanoparticles is given in Biotechnol. Prog., 19:1095-100 (2003), J. Am. Chem. Soc. 125:9828-33 (2003), J. Colloid Interface Sci. 255:293-8 (2002).

In some embodiments, the nanoparticle or its ligand comprises a detectable label. The label may be an element of the core of the nanoparticle or the ligand. The label may be detectable because of an intrinsic property of that element of the nanoparticle or by being linked, conjugated or associated with a further moiety that is detectable. Preferred examples of labels include a label which is a fluorescent group, a radionuclide, a magnetic label or a dye. Fluorescent groups include fluorescein, rhodamine or tetramethyl rhodamine, Texas-Red, Cy3, Cy5, etc., and may be detected by excitation of the fluorescent label and detection of the emitted light using Raman scattering spectroscopy (Y. C. Cao, R. Jin, C. A. Mirkin, Science 2002, 297: 1536-1539).

In some embodiments, the nanoparticles may comprise a radionuclide for use in detecting the nanoparticle using the radioactivity emitted by the radionuclide, e.g. by using PET, SPECT, or for therapy, i.e. for killing target cells. Examples of radionuclides commonly used in the art that could be readily adapted for use in the present invention include $^{99m}Tc$, which exists in a variety of oxidation states although the most stable is $TcO^{-4}$; $^{32}P$ or $^{33}P$; $^{57}Co$; $^{59}Fe$; $^{67}Cu$ which is often used as $Cu^{2+}$ salts; $^{67}Ga$ which is commonly used a $Ga^{3+}$ salt, e.g. gallium citrate; $^{68}Ge$; $^{82}Sr$; $^{99}Mo$; $^{103}Pd$; $^{111}In$ which is generally used as $In^{3+}$ salts; $^{125}I$ or $^{131}I$ which is generally used as sodium iodide; $^{137}Cs$; $^{153}Gd$; $^{183}Sm$; $^{158}Au$; $^{186}Re$; $^{201}Tl$ generally used as a $Tl^+$ salt such as thallium chloride; $^{39}Y^{3+}$; $^{71}Lu^{3+}$; and $^{24}Cr^{2+}$. The general use of radionuclides as labels and tracers is well known in the art and could readily be adapted by the skilled person for use in the aspects of the present invention. The radionuclides may be employed most easily by doping the cores of the nanoparticles or including them as labels present as part of ligands immobilised on the nanoparticles.

Additionally or alternatively, the nanoparticles of the present invention, or the results of their interactions with other species, can be detected using a number of techniques well known in the art using a label associated with the nanoparticle as indicated above or by employing a property of them. These methods of detecting nanoparticles can range from detecting the aggregation that results when the nanoparticles bind to another species, e.g. by simple visual inspection or by using light scattering (transmittance of a solution containing the nanoparticles), to using sophisticated techniques such as transmission electron microscopy (TEM) or atomic force microscopy (AFM) to visualise the nanoparticles. A further method of detecting metal particles is to employ plasmon resonance that is the excitation of electrons at the surface of a metal, usually caused by optical radiation. The phenomenon of surface plasmon resonance (SPR) exists at the interface of a metal (such as Ag or Au) and a dielectric material such as air or water. As changes in SPR occur as analytes bind to the ligand immobilised on the surface of a nanoparticle changing the refractive index of the interface. A further advantage of SPR is that it can be used to monitor real time interactions. As mentioned above, if the nanoparticles include or are doped with atoms which are NMR active, then this technique can be used to detect the particles, both in vitro or in vivo, using techniques well known in the art. Nanoparticles can also be detected using a system based on quantitative signal amplification using the nanoparticle-promoted reduction of silver (I). Fluorescence spectroscopy can be used if the nanoparticles include ligands as fluorescent probes. Also, isotopic labelling of the carbohydrate can be used to facilitate their detection.

Insulin Peptide Analogues

In certain cases in accordance with the present invention, the "insulin analogue" may be any derivative of, mutant form of, or synthetic mimic of, insulin. In particular the insulin analogue may comprise or consist of an amino acid A chain having at least 70%, 80%, 90%, 95% or 99% amino acid sequence identity with the full-length amino acid sequence set forth as SEQ ID NO: 1 and an amino acid B chain having at least 70%, 80%, 90%, 95% or 99% amino acid sequence identity with any one of the full-length amino acid sequences set forth as SEQ ID NOS: 2-5, wherein the A and B chains are linked. In some cases, the link between the A and B chains comprises at least one or at least two disulphide bonds. In some cases, the analogue of insulin comprises an A chain that has up to 1, 2, 3, 4 or 5 amino acid changes by substitution, addition and/or deletion as compared with the full-length A chain amino acid sequence set forth in SEQ ID NO: 1. In some cases, the analogue of insulin comprises a B chain that has up to 1, 2, 3, 4 or 5 amino acid changes by substitution, addition and/or deletion as compared with any one of the full-length B chain amino acid sequences set forth in SEQ ID NOS: 2-5.

The human insulin sequence is disclosed at UniProt accession no. P01308, version 186, dated 13 Nov. 2013. Human insulin is a heterodimer of insulin A chain and insulin B chain linked by two disulphide bonds.

The A chain (consisting of residues 90-110 of the 110 amino acid sequence of preproinsulin) has the following sequence:

```
>sp|P01308|90-110
GIVEQCCTSICSLYQLENYCN        (SEQ ID NO: 1)
```

The B chain (consisting of residues 25-54 of the 110 amino acid sequence of preproinsulin) has the following sequence:

```
>sp|P01308|25-54
FVNQHLCGSHLVEALYLVCGERGFFYTPKT  (SEQ ID NO: 2)
```

The A and B chains are linked by two disulphide bonds: a first interchain bond between Cys31 of the B chain and Cys 96 of the A chain (numbered according to the preproinsulin sequence) and a second interchain bond between Cys43 of the B chain and Cys109 of the A chain (numbered according to the preproinsulin sequence).

In some cases in accordance with any aspect of the present invention, the analogue of insulin may be a fast-acting insulin analogue. In particular, the insulin analogue may be selected from the group consisting of: insulin lispro (Humalog®, Eli Lilly and Company), insulin aspart (NovoRapid®, Novo Nordisk A/S) and insulin glulisine (Apidra®, Sanofi-Aventis).

Insulin lispro is a fast-acting insulin analogue having an inversion of Lys28 and Pro29 of the B chain compared with native insulin (i.e. positions 52 and 53 numbered according to the preproinsulin sequence). The B chain of insulin lispro therefore has the amino acid sequence FVNQHLCG-SHLVEALYLVCGERGFFYT<u>KP</u>T (SEQ ID NO: 3).

Insulin aspart is a fast-acting insulin analogue having the amino acid substitution Pro28Asp in the B chain compared with native insulin (i.e. position 52 numbered according to the preproinsulin sequence). The B chain of insulin aspart therefore has the amino acid sequence FVNQHLCG-SHLVEALYLVCGERGFFYT<u>D</u>KT (SEQ ID NO: 4).

Insulin glulisine is a fast-acting insulin analogue having the amino acid substitutions Asn3Lys and Lys29Glu in the B chain compared with native insulin (i.e. positions 27 and 53 numbered according to the preproinsulin sequence). The B chain of insulin glulisine therefore has the amino acid sequence FV<u>K</u>QHLCGSHLVEALYLVCGERGFFYTP<u>ET</u> (SEQ ID NO: 5).

Sequence identity may be calculated using any suitable method, as would be readily apparent to the skilled person. In certain cases, amino acid sequence identity between a candidate sequence and a reference sequence, e.g. the sequence of SEQ ID NO: 1, may be calculated using the online tool SUPERMATCHER available at the following URL: emboss-.bioinformatics.nl/cgi-bin/emboss/supermatcher using GAP opening penalty of 10.0 and GAP extension penalty of 0.5 (see EMBOSS: The European Molecular Biology Open Software Suite (2000) Rice, P. Longden, I. and Bleasby, A. *Trends in Genetics* 16, (6) pp. 276-277).

Administration and Treatment

The nanoparticles and compositions of the invention may be administered to patients by any number of different routes, including enteral or parenteral routes. Parenteral administration includes administration by the following routes: intravenous, cutaneous or subcutaneous, nasal, intramuscular, intraocular, transepithelial, intraperitoneal and topical (including dermal, ocular, rectal, nasal, inhalation and aerosol), film, patch and rectal systemic routes. In some cases the nanoparticles and compositions of the invention may be administered or formulated for administration via transbuccal route.

Administration be performed e.g. by injection, or ballistically using a delivery gun to accelerate their transdermal passage through the outer layer of the epidermis. The nanoparticles may also be delivered in aerosols. This is made possible by the small size of the nanoparticles.

The nanoparticles of the invention may be formulated as pharmaceutical compositions that may be in the forms of solid or liquid compositions. In some cases the nanoparticles may be formulated in a viscoelastic film, e.g. for transbuccal delivery. Compositions in accordance with the present invention will generally comprise a carrier of some sort, for example a solid carrier or a liquid carrier such as water, petroleum, animal or vegetable oils, mineral oil or synthetic oil. Physiological saline solution, or glycols such as ethylene glycol, propylene glycol or polyethylene glycol may be included. Such compositions and preparations generally contain at least 0.1 wt % of the compound.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, solutions of the compounds or a derivative thereof, e.g. in physiological saline, a dispersion prepared with glycerol, liquid polyethylene glycol or oils.

In addition to one or more of the compounds, optionally in combination with other active ingredient, the compositions can comprise one or more of a pharmaceutically acceptable excipient, carrier, buffer, stabiliser, isotonicising agent, preservative or anti-oxidant or other materials well known to those skilled in the art. Such materials should be non-toxic and should not interfere with the efficacy of the active ingredient. The precise nature of the carrier or other material may depend on the route of administration, e.g. intravenously, orally or parenterally.

Liquid pharmaceutical compositions are typically formulated to have a pH between about 3.0 and 9.0, more preferably between about 4.5 and 8.5 and still more preferably between about 5.0 and 8.0. The pH of a composition can be maintained by the use of a buffer such as acetate, citrate, phosphate, succinate, Tris or histidine, typically employed in the range from about 1 mM to 50 mM. The pH of compositions can otherwise be adjusted by using physiologically acceptable acids or bases.

Preservatives are generally included in pharmaceutical compositions to retard microbial growth, extending the shelf life of the compositions and allowing multiple use packaging. Examples of preservatives include phenol, meta-cresol, benzyl alcohol, para-hydroxybenzoic acid and its esters, methyl paraben, propyl paraben, benzalconium chloride and benzethonium chloride. Preservatives are typically employed in the range of about 0.1 to 1.0% (w/v).

Preferably, the pharmaceutically compositions are given to an individual in a prophylactically effective amount or a therapeutically effective amount (as the case may be, although prophylaxis may be considered therapy), this being sufficient to show benefit to the individual. Typically, this will be to cause a therapeutically useful activity providing benefit to the individual. The actual amount of the compounds administered, and rate and time-course of administration, will depend on the nature and severity of the condition being treated. Prescription of treatment, e.g. decisions on dosage etc., is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Handbook of Pharmaceutical Additives, 2nd Edition (eds. M. Ash and I. Ash), 2001 (Synapse Information Resources, Inc., Endicott, N.Y., USA); Remington's Pharmaceutical Sciences, 20th Edition, 2000, pub. Lippincott, Williams & Wilkins; and Handbook of Pharmaceutical Excipients, 2nd edition, 1994. By way of example, and the compositions are preferably administered to patients in dosages of between about 0.01 and 100 mg of active compound per kg of body weight, and more preferably between about 0.5 and 10 mg/kg of body weight.

The following is presented by way of example and is not to be construed as a limitation to the scope of the claims.

EXAMPLES

Example 1

Synthesis of Nanoparticles

Synthesis of gold nanoparticles having a corona comprising, e.g., carbohydrate ligands has been described previously (WO 2011/154711; and Lund et al., 2011, Biomaterials Vol. 32 pp. 9776-9784, the entire contents of which are expressly incorporated herein by reference).

Briefly, preparation of amine alpha-gal gold nanoparticles involved the following procedure: To a mix of amine-mercapto hexaethylenglycol linker (structure 6 in WO 2011/154711) and alpha-galactose ligand (structure 3 in WO 2011/154711) in a ratio 1:1 (0.58 mmol, 3 eq.) in MeOH (49 mL) was added an aqueous solution of gold salt (7.86 mL, 0.19 mmol, 0.025M). The reaction was stirred during 30 seconds and then, an aqueous solution of NaBH4 (1N) was added in several portions (4.32 mL, 4.32 mmol). The reaction was shaken for 100 minutes at 900 rpm. After this time, the suspension was centrifuged 1 minute at 14000 rpm. The supernatant is removed and the precipitated was dissolved in 2 mL of water. Then, 2 mL of the suspension were introduced in two filters (AMICON, 10 KDa, 4 mL) and were centrifuged 5 minutes at 4500 g. The residue in the filter was washed twice more with water. The final residue was dissolved in 80 mL of water.

A schematic representation of the resulting nanoparticles having a plurality of ligands in the ratio 1:1 of alpha-Gal:EG6NH2 "NP-alpha-Gal(1)EG6MH2(1)" is shown in FIG. 11 of WO 2011/154711.

For the preparation of gold NPs manufacture was under laminar flow cabinet. All glass and plastic material (such as eppendorfs, vials and bottles) and solvent (water, HAc) were first sterilized in an autoclave. All other disposables (such as tips and filters) came pre-sterilized.

Binding of insulin and/or insulin analogue peptides to the nanoparticle corona was achieved essentially as described in Example 3 of WO 2011/154711.

Example 2

Glucose and Counter-Hormone Response to Free and to Nanoparticle-Bound Insulin and Insulin Analogues In Vivo In order to explore further the effects of nanoparticle-bound insulin and analogues thereof on glycemic regulation in vivo and to compare and contrast with subcutaneously delivered, rapidly-acting insulin analogues administered as free peptide (i.e. not bound to nanoparticles), test items were administered to minipigs and pharmacodynamics responses evaluated. Animals were fasted overnight and then placed under anaesthesia.

Minipig plasma glucose was monitored over time and responses to free insulin lispro and to gold nanoparticle-bound insulin measured. Glucose concentration is shown plotted against time for 1.2 U/kg gold nanoparticle-bound insulin ("GNP-I"; filled squares); 0.3 U/kg GNPI (filled triangles); and 1.2 U/kg free insulin lispro (filled circles). The results indicate that for equal subcutaneous (s.c.) dose of analogue insulin lispro and GNP-regular insulin the analogue insulin lispro results in hypoglycemia relative to nanoparticle-bound insulin.

Figure 2A:
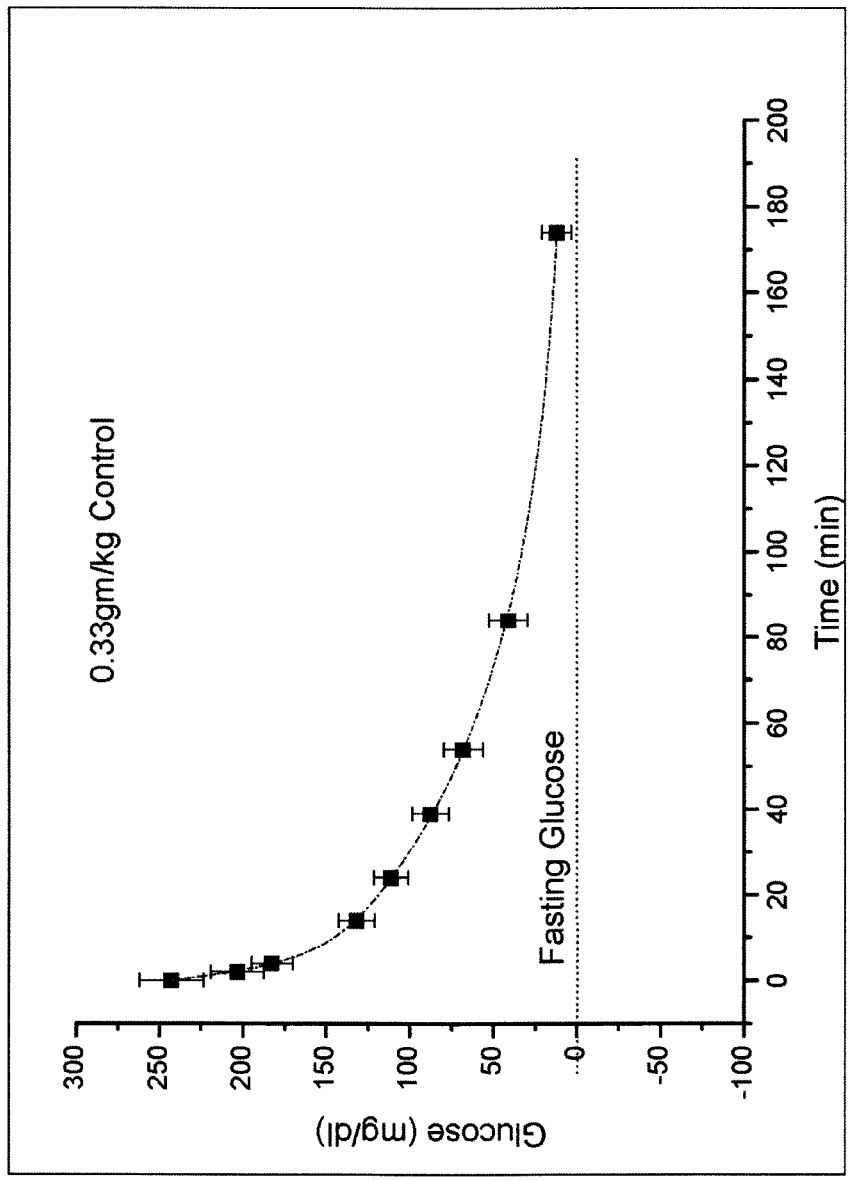
FIG. 2A-FIG. 2D shows blood glucose clearance rates in minipigs.
Figure 2B:
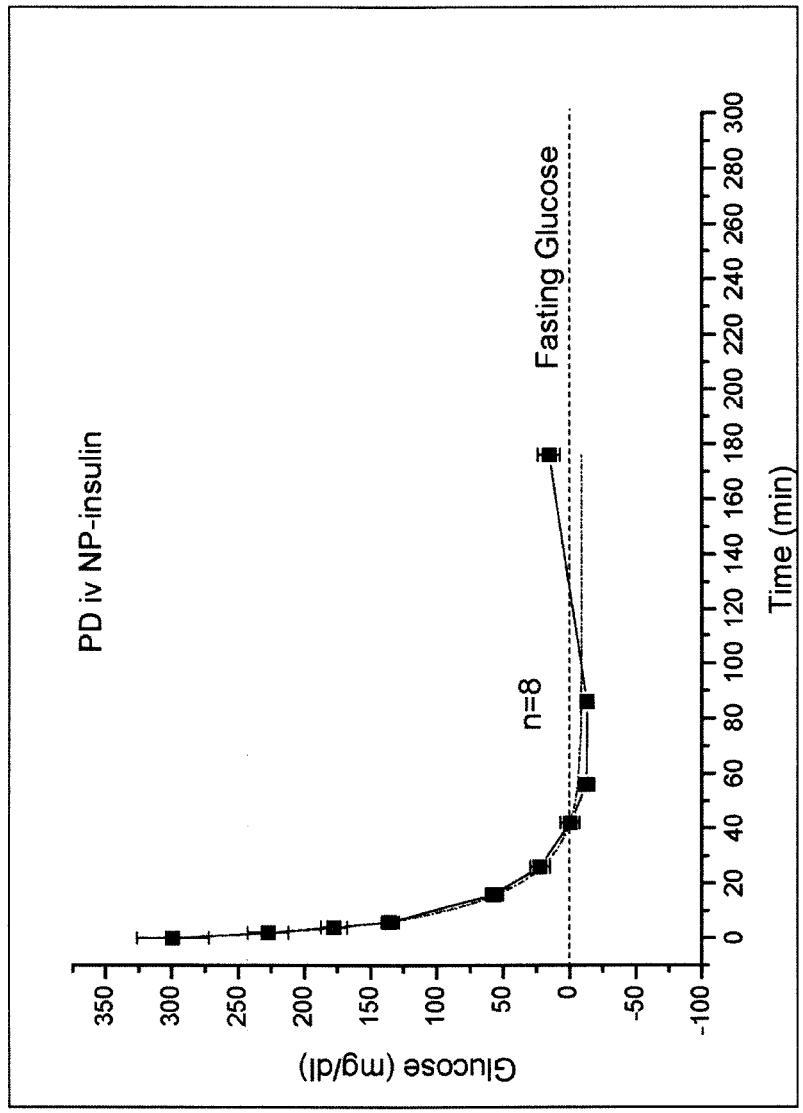
Figure 2C:
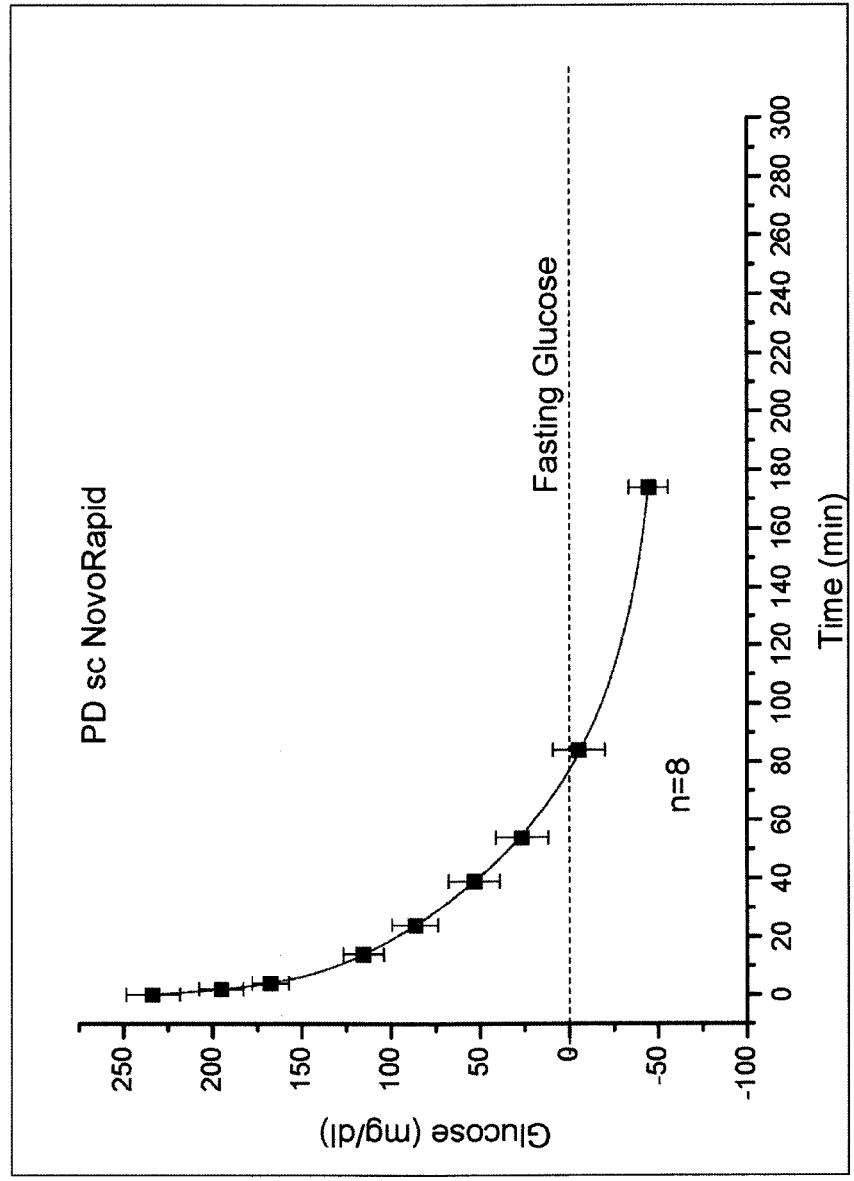
Figure 2D:
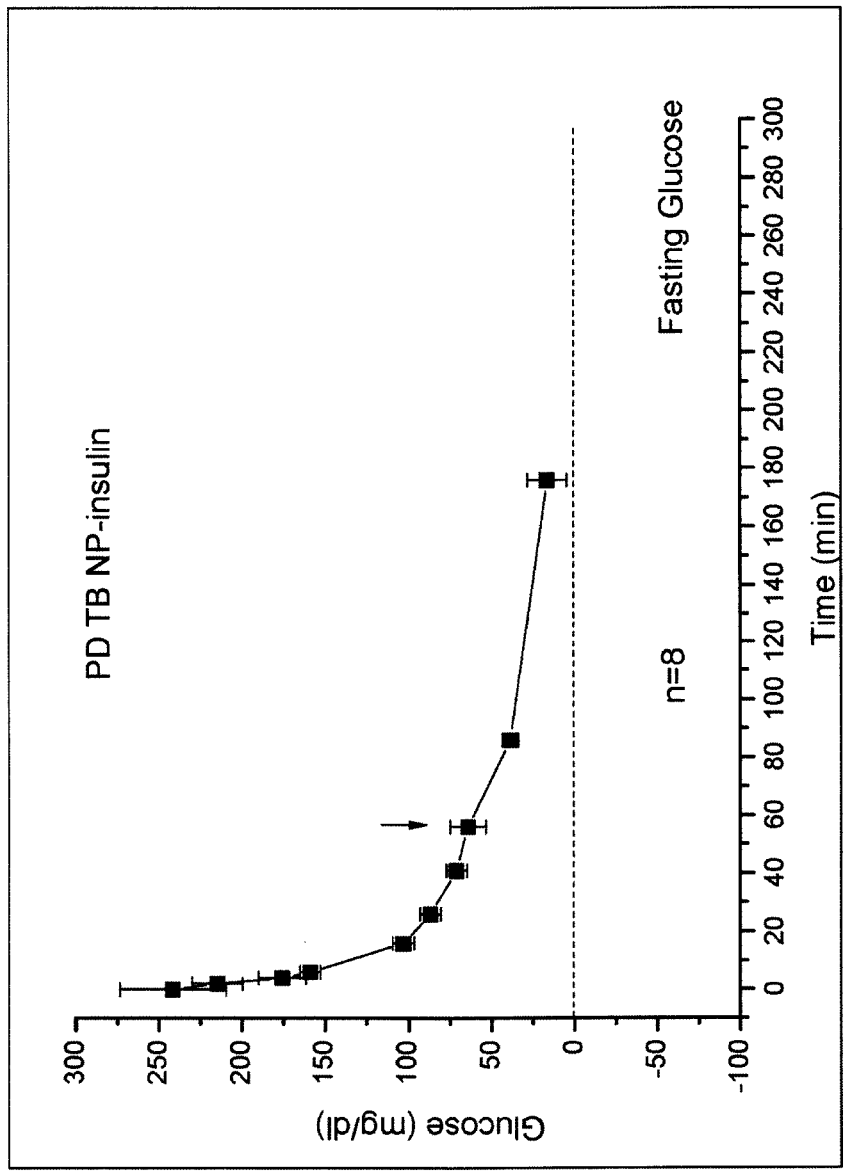

Blood glucose clearance rates were evaluated in minipigs following administration of various control or test items. FIG. 2A shows results from control animals receiving no insulin; FIG. 2B shows results from test animals receiving intravenous (i.v.) nanoparticle-bound insulin; FIG. 2C shows results from control animals receiving 2.5 units of subcutaneous (s.c.) NovoRapid® insulin aspart; FIG. 2D shows results from test animals receiving transbuccal GNP-regular insulin formulated in PharmFilm™. Each of these curves can be transformed, and early (K1), and late (K2) rate constants for glucose clearance calculated. The results show hypoglycemia for s.c. NovoRapid® (see FIG. 2C), but no hypoglycemia for nanoparticle-bound insulin (see FIG. 2B and FIG. 2D).

Figure 3A:
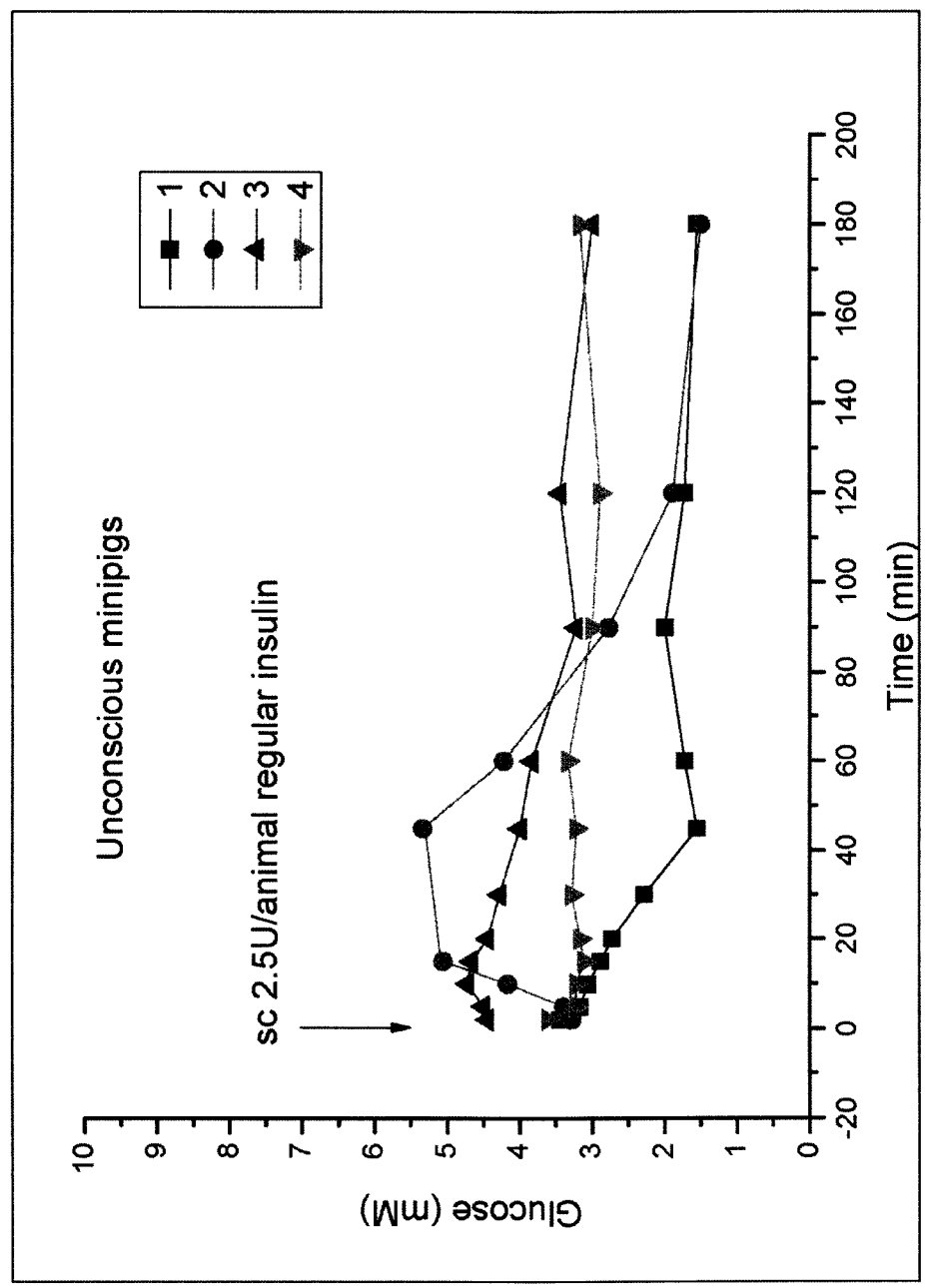
FIG. 3A-FIG. 3C shows the effect of subcutaneous (s.c.) injection of insulin in an insulin stress test.
Figure 3B:
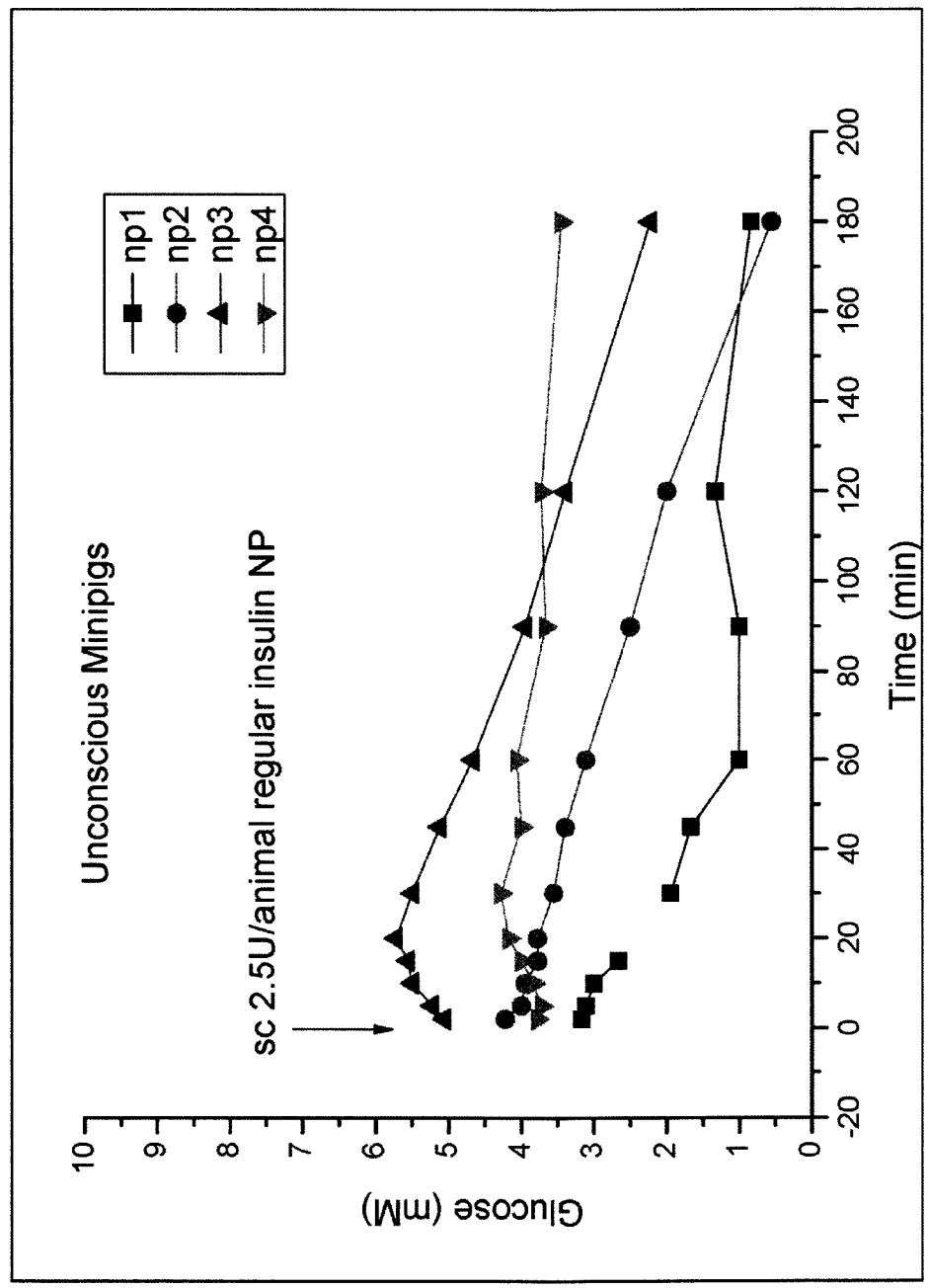
Figure 3C:
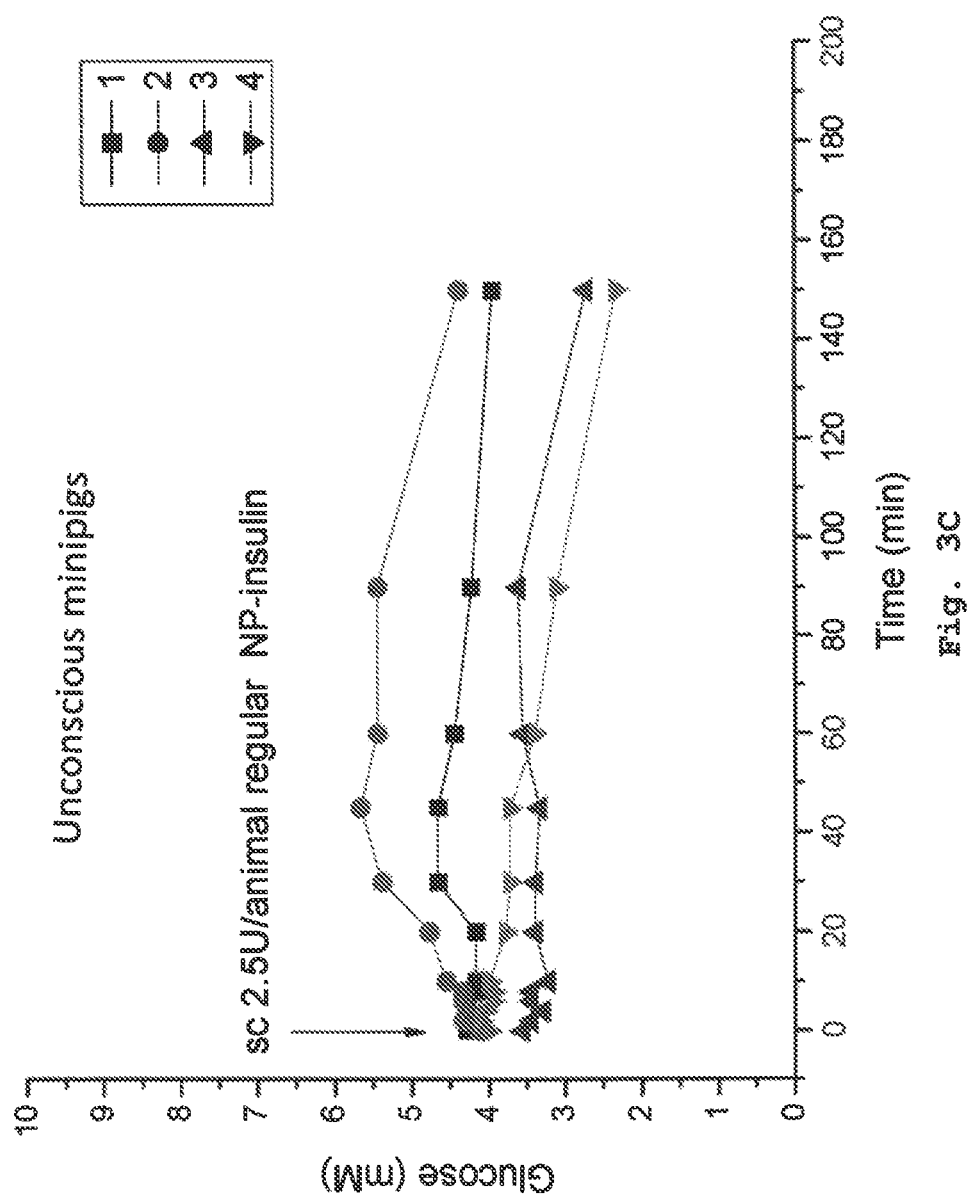

Next, the effect of subcutaneous (s.c.) injection of insulin in an insulin stress test was evaluated. FIG. 3A shows results from a s.c. injection of 2.5 U/animal regular (Diosynth) free insulin upon administration to anaesthetized minipigs (1-squares; 2-circles; 3-triangles; and 4-inverted triangles) and blood glucose concentration plotted against time. FIG. 3B shows results from a s.c. injection of 2.5 U/animal gold nanoparticle (GNP)-bound regular (Diosynth) insulin following administration to anaesthetized minipigs (1-squares; 2-circles; 3-triangles; and 4-inverted triangles) and blood glucose concentration plotted against time. FIG. 3C shows results from a s.c. injection of 2.5 U/animal gold nanoparticle (GNP)-bound regular (Diosynth) insulin administered to anaesthetized minipigs (1-squares; 2-circles; 3-triangles; and 4-inverted triangles) with blood glucose concentration plotted against time. The results show that in these insulin stress tests neither s.c. administration of regular insulin or GNP-I insulin results in hypoglycemia.

Figure 4:
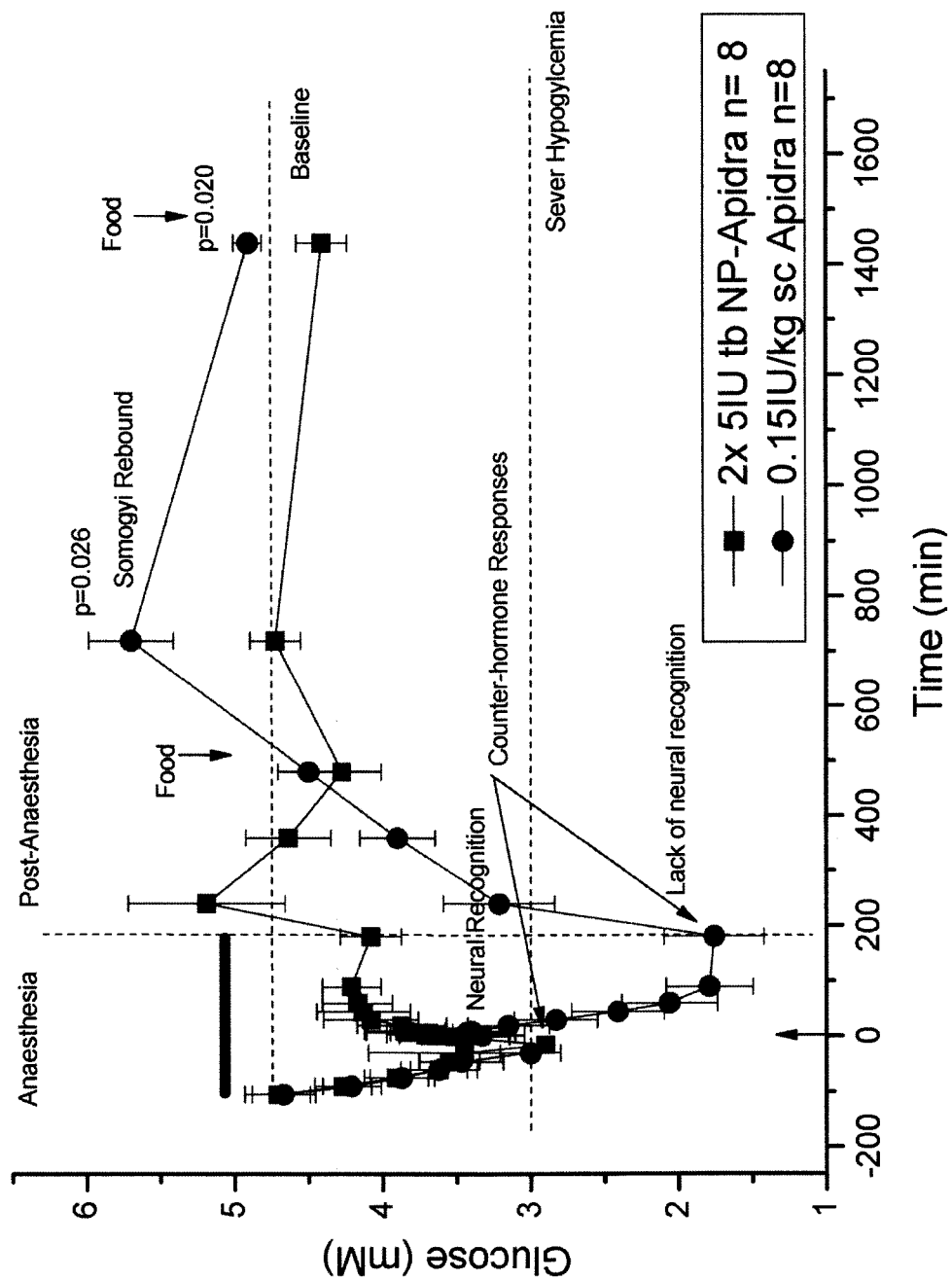
FIG. 4 shows an insulin stress test following s.c. injection of 0.15 IU/kg free Apidra® (analogue insulin glulisine; circles; n=8) or transbuccal delivery of gold nanoparticle (GNP)-bound Apidra® (analogue insulin glulisine; squares; n=8) in anesthetized minipigs. Blood glucose concentration is plotted against time. Significant features of the glucose response patterns are indicated. These results show that s.c. administration of the rapidly-acting insulin analogue Apidra® results in hypoglycemia, whereas transbuccal administration of GNP-bound Apidra® does not exhibit hypoglycemia.

In a further experiment, the pharmacodynamics response to transbuccal nanoparticle-bound Apidra® was evaluated in anaesthetised minipigs and compared with the response to free Apidra®. FIG. 4 shows an insulin stress test following s.c. injection of 0.15 IU/kg free Apidra® (analogue insulin glulisine; circles; n=8) or transbuccal delivery of gold nanoparticle (GNP)-bound Apidra® (analogue insulin glulisine; squares; n=8) in anesthetized minipigs. Blood glucose concentration is plotted against time. Significant features of the glucose response patterns are indicated (e.g. the lack of neural recognition of hypoglycemia and lack of counter-hormone responses are shown on the free Apridra® trace). These results show that s.c. administration of the rapidly-acting insulin analogue Apidra® results in hypoglycemia, whereas transbuccal administration of GNP-bound Apidra® does not exhibit hypoglycemia.

Figure 5A:
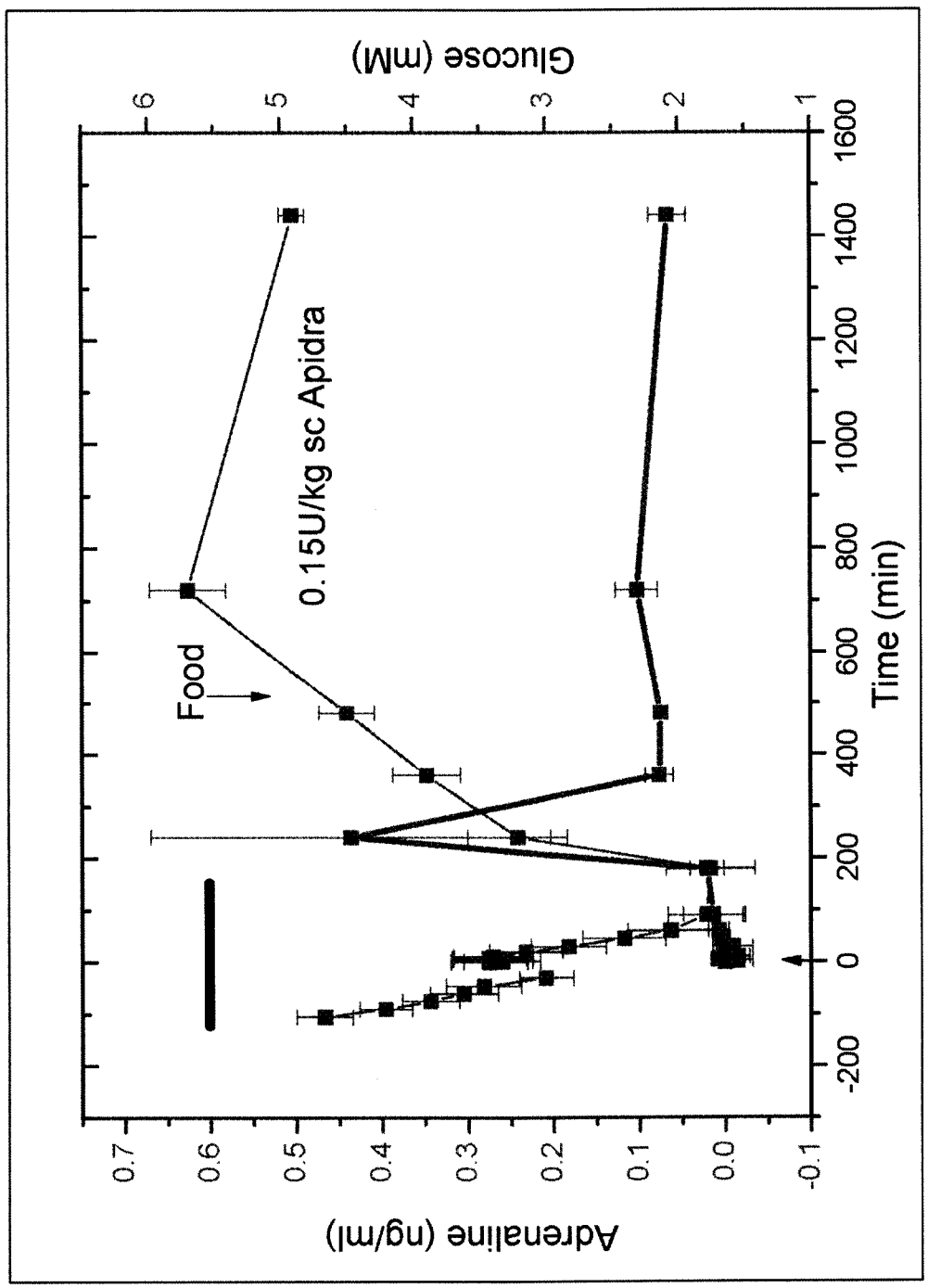
FIG. 5A-FIG. 5C shows that s.c. Apidra® does not induce counter-hormones during anaesthesia.
Figure 5B:
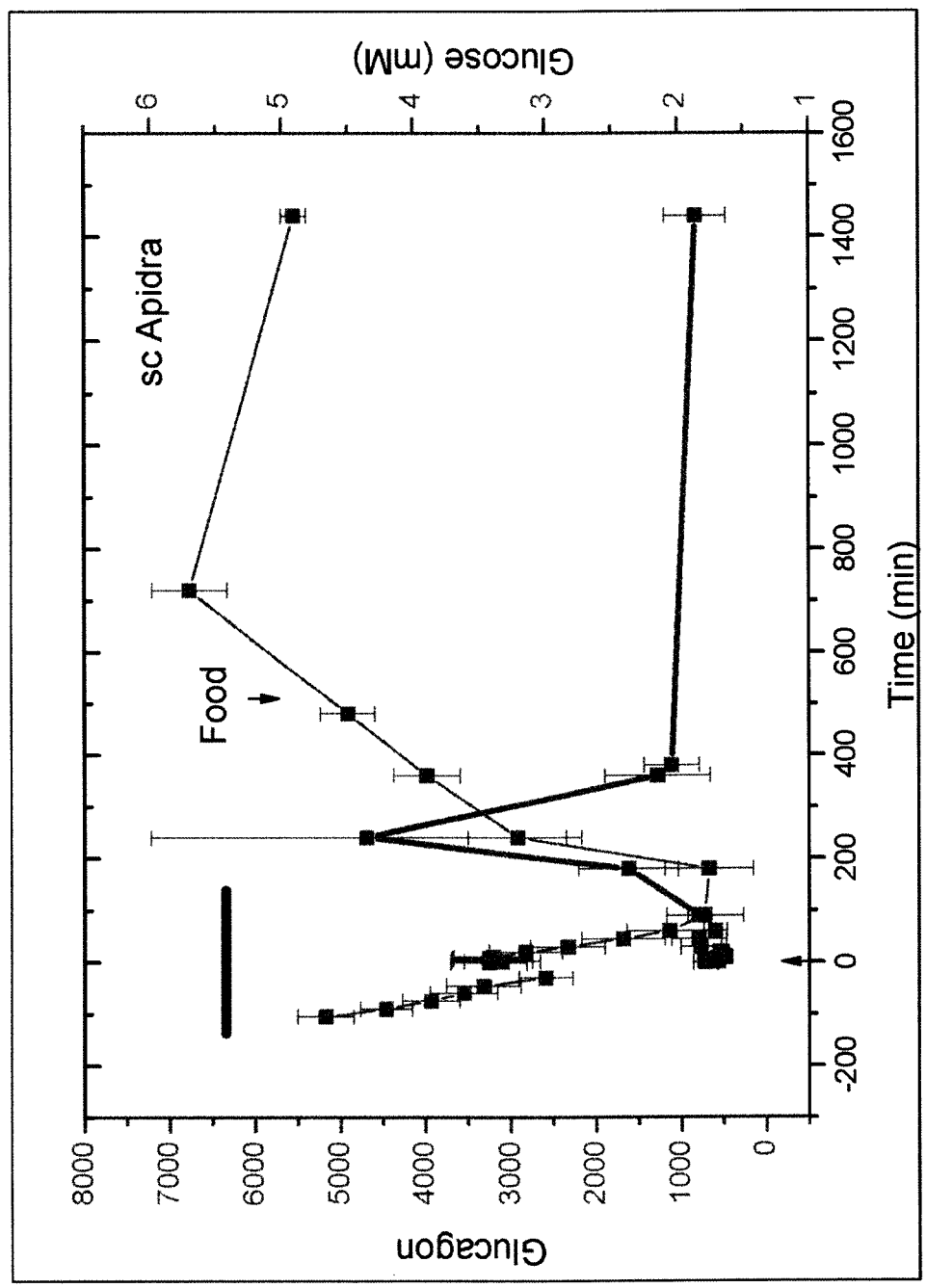
Figure 5C:
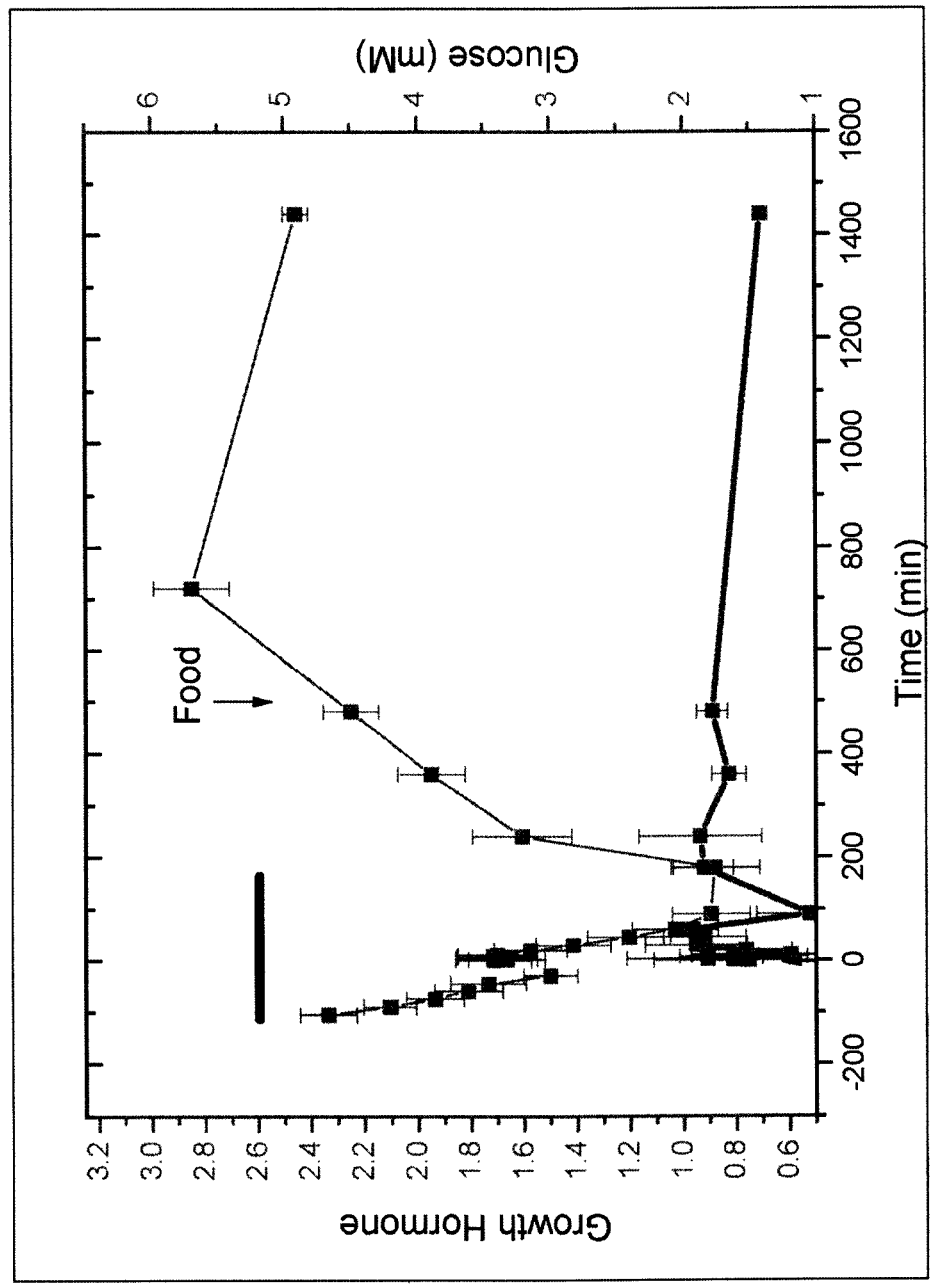

In a further experiment the possibility of induction of counter-hormone responses by s.c. administration of free Apidra® was investigated. FIG. 5A-FIG. 5C show that s.c. free Apridra® does not induce counter-hormones during anaesthesia. FIG. 5A: adrenalin (left-hand y-axis) and glucose (right-hand y-axis) concentrations are plotted against time for 0.15 U/kg s.c. administered Apidra® in anaesthetised minipigs; FIG. 5B: glucagon (left-hand y-axis) and glucose (right-hand y-axis) concentrations are plotted against time for 0.15 U/kg s.c. administered Apidra® in anaesthetised minipigs; and FIG. 5C growth hormone (left-hand y-axis) and glucose (right-hand y-axis) concentrations are plotted against time for 0.15 U/kg s.c. administered Apidra® in anaesthetised minipigs. The results show that, despite induction of hypoglycemia, the Apidra® does not generate a counter-hormone response. S.c. administered Apidra® only induces counter-hormone release post-anesthesia; there is no induction of early hypoglycemia recognition.

Figure 6A:
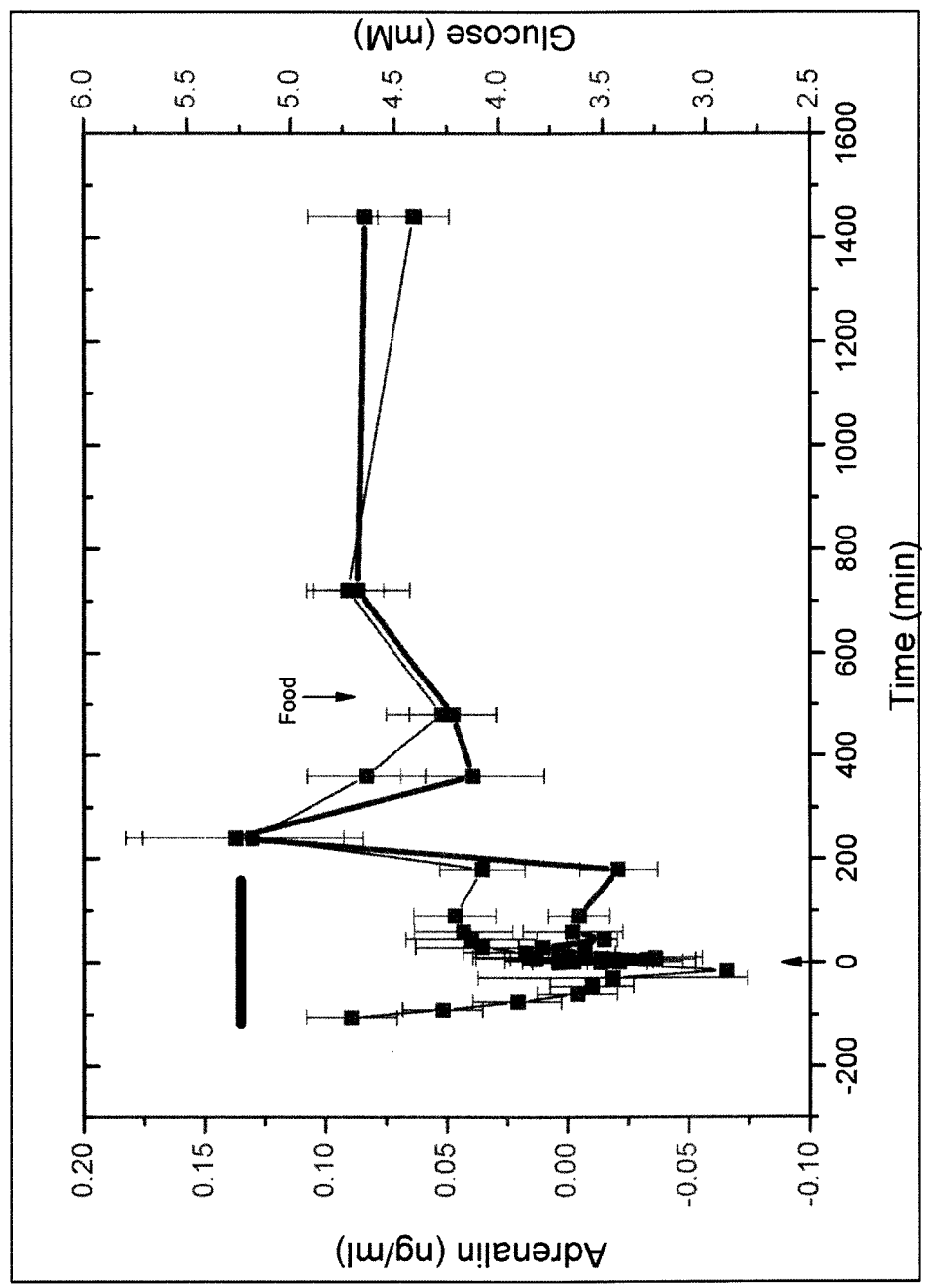
FIG. 6A-FIG. 6B shows that transbuccally administered gold nanoparticle-bound Apidra® triggers a neural counter-hormone response in an insulin stress test in minipigs.
Figure 6B:
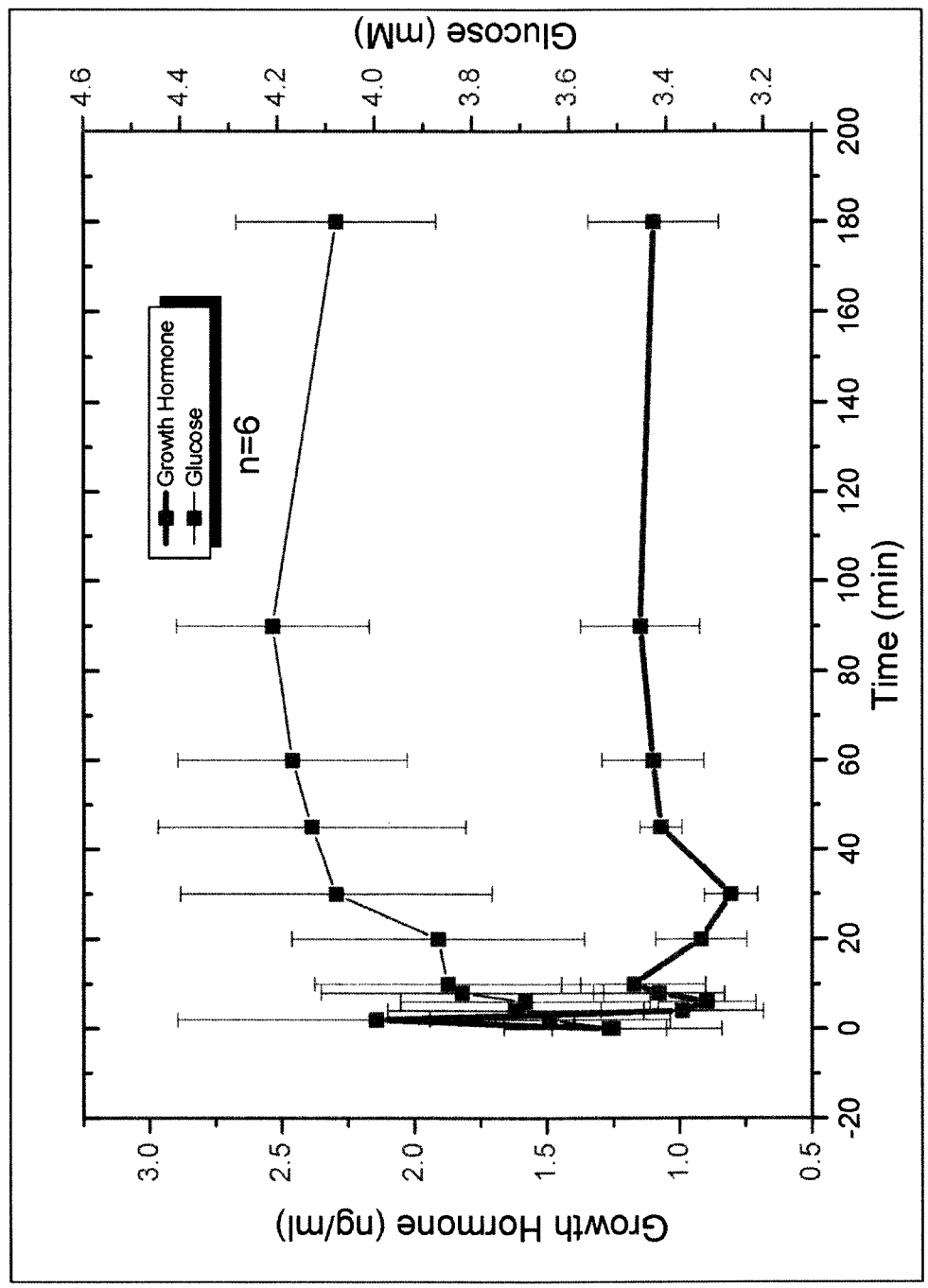

In a further experiment the possibility of induction of counter-hormone responses by transbuccally administered gold nanoparticle-bound Apridra® was investigated. FIG. 6A and FIG. 6B show that transbuccally administered gold nanoparticle-bound Apridra® triggers a neural counter-hormone response in an insulin stress test in minipigs. FIG. 6A: adrenalin (left-hand y-axis) and glucose (right-hand y-axis) concentrations are plotted against time for transbuccally administered, gold nanoparticle-bound Apidra® (TB-GNP-Apidra®); FIG. 6B: growth hormone (GH) (left-hand y-axis) and glucose (right-hand y-axis) concentrations are plotted against time for transbuccally administered, gold nanoparticle-bound Apidra® (TB-GNP-Apidra®). The observed immediate rise of plasma adrenalin and GH to TB-GNP-Apidra® could explain the quick rise in blood glucose post-TB-GNP-Apidra® administration.

All references cited herein are incorporated herein by reference in their entirety and for all purposes to the same extent as if each individual publication or patent or patent application was specifically and individually indicated to be incorporated by reference in its entirety.

The specific embodiments described herein are offered by way of example, not by way of limitation. Any sub-titles herein are included for convenience only, and are not to be construed as limiting the disclosure in any way.

The invention claimed is:

1. A pharmaceutical composition comprising:
   (i) a free insulin analogue peptide selected from the group consisting of: insulin lispro, insulin aspart, and insulin glulisine; and
   (ii) a plurality of nanoparticles, each of said nanoparticles comprising:
      (a) a core comprising a metal and/or a semiconductor;
      (b) a corona comprising a plurality of ligands covalently linked to the core, wherein at least one of said ligands comprises a carbohydrate moiety; and
      (c) at least one insulin non-covalently bound to the corona,
   wherein the molar ratio of free insulin analogue peptide to the nanoparticle-bound insulin is in the range 1:1 to 100:1, and wherein the nanoparticle-bound insulin induces an increase in plasma adrenalin concentration and/or plasma growth hormone concentration upon administration to a mammalian subject.

2. The pharmaceutical composition according to claim 1, wherein the free insulin analogue peptide is insulin glulisine.

3. A method of regulating blood glucose concentration in a diabetic or pre-diabetic mammalian subject, said method comprising administering to the subject an effective amount of the pharmaceutical composition according to claim 1.

4. A method of reducing the incidence of hypoglycemic adverse events in an insulin-dependent diabetic or pre-diabetic mammalian subject, said method comprising:
   administering, simultaneously, sequentially or concurrently with a dose of a free insulin analogue peptide selected from the group consisting of: insulin lispro, insulin aspart, and insulin glulisine, an effective amount of a pharmaceutical composition comprising a plurality of nanoparticles, each of said nanoparticles comprising:
      (a) a core comprising a metal and/or a semiconductor;
      (b) a corona comprising a plurality of ligands covalently linked to the core, wherein at least one of said ligands comprises a carbohydrate moiety; and
      (c) at least one insulin non-covalently bound to the corona.

5. The method according to claim 4, wherein administration is sequential, and wherein the dose of free insulin analogue peptide is administered prior to or after said effective amount of said pharmaceutical composition comprising the plurality of nanoparticles.

6. The method according to claim 5, wherein the dose of free insulin analogue peptide and the effective amount of said pharmaceutical composition comprising the plurality of nanoparticles are administered between 1 second and 1 hour apart.

7. The pharmaceutical composition of claim 1, wherein the average number of nanoparticle-bound insulins per nanoparticle core is at least 2.

8. The pharmaceutical composition of claim 1, wherein said at least one ligand comprising a carbohydrate moiety is selected from the group consisting of: 2'-thioethyl-α-D-galactopyranoside, 2'-thioethyl-β-D-glucopyranoside, 2'-thioethyl-2-acetamido-2-deoxy-β-D-glucopyranoside, 5'-thiopentanyl-2-deoxy-2-imidazolacetamido-α,β-D-glucopyranoside and 2'-thioethyl-α-D-glucopyranoside, wherein said at least one ligand comprising a carbohydrate moiety is covalently linked to the core via its sulphur atom.

9. The pharmaceutical composition of claim 8, wherein said plurality of ligands covalently linked to the core comprises at least a first ligand and a second ligand, wherein the first and second ligands are different.

10. The pharmaceutical composition of claim 9, wherein:
(a) said first ligand comprises 2'-thioethyl-α-D-galactopyranoside and said second ligand comprises 1-amino-17-mercapto-3,6,9,12,15,-pentaoxa-heptadecanol;
(b) said first ligand comprises 2'-thioethyl-β-D-glucopyranoside or 2'-thioethyl-α-D-glucopyranoside and said second ligand comprises 5'-thiopentanyl-2-deoxy-2-imidazolacetamido-α,β-D-glucopyranoside;
(c) said first ligand comprises 2'-thioethyl-β-D-glucopyranoside or 2'-thioethyl-α-D-glucopyranoside and said second ligand comprises 1-amino-17-mercapto-3,6,9,12,15,-pentaoxa-heptadecanol; or
(d) said first ligand comprises 2'-thioethyl-2-acetamido-2-deoxy-β-D-glucopyranoside and said second ligand comprises 1-amino-17-mercapto-3,6,9,12,15,-pentaoxa-heptadecanol, and wherein said first and second ligands are covalently linked to the core via their respective sulphur atoms.

11. The pharmaceutical composition of claim 1, wherein the nanoparticle comprises a component having a divalent state.

12. The pharmaceutical composition of claim 11, wherein said component having a divalent state is $Zn^{2+}$.

13. The pharmaceutical composition of claim 1, wherein said plurality of nanoparticles are formulated in a carrier, a solution, a polymer, a powder, or a cream, in which the nanoparticles and bound insulin are suspended and/or embedded.

14. The pharmaceutical composition of claim 13, wherein the nanoparticle formulation is in the form of a patch or film for delivery to or across skin, mouth, cheek, vagina, or rectum or in the form of a spray for delivery into the mouth, nose, lungs, rectum or vagina.

15. The pharmaceutical composition of claim 1, wherein the nanoparticles having insulin bound thereto and the free insulin analogue peptide are in a single package, container or carrier.

16. An article of manufacture comprising:
a pharmaceutical composition as defined in claim 1;
a container for housing the pharmaceutical composition; and
an insert and/or label.

17. The article of manufacture according to claim 16, wherein the insert and/or label provide instructions, dosage and/or administration information relating to the use of the pharmaceutical composition in a method of managing blood glucose concentration, glycemic control and/or a method of managing or treating diabetes.

18. A process for producing a pharmaceutical composition as defined in claim 1, comprising:
providing a nanoparticle comprising a core comprising a metal and/or a semiconductor and a corona comprising a plurality of ligands covalently linked to the core, wherein said ligands comprise one or more carbohydrate moieties;
contacting the nanoparticle with at least one insulin under conditions which allow the at least one insulin to bind to the corona of the nanoparticle; and
combining the resulting nanoparticle having insulin bound thereto with free insulin analogue peptide that is not bound to a nanoparticle, said free insulin analogue peptide being selected from the group consisting of: insulin lispro, insulin aspart, and insulin glulisine.

19. A pharmaceutical composition comprising:
(i) a free insulin analogue peptide selected from the group consisting of: insulin lispro, insulin aspart, and insulin glulisine; and
(ii) a plurality of nanoparticles, each of said nanoparticles comprising:
(a) a core comprising a metal and/or a semiconductor;
(b) a corona comprising a plurality of ligands covalently linked to the core, wherein at least one of said ligands comprises a carbohydrate moiety; and
(c) at least one insulin analogue peptide selected from the group consisting of: insulin lispro, insulin aspart, and insulin glulisine, said insulin analogue peptide being non-covalently bound to the corona,
wherein the molar ratio of free insulin analogue peptide to the nanoparticle-bound insulin analogue peptide is in the range 1:1 to 100:1,
and wherein the nanoparticle-bound insulin analogue peptide induces an increase in plasma adrenalin concentration and/or plasma growth hormone concentration upon administration to a mammalian subject.

* * * * *

```
                        SEQUENCE LISTING

<160> NUMBER OF SEQ ID NOS: 5

<210> SEQ ID NO 1
<211> LENGTH: 21
<212> TYPE: PRT
<213> ORGANISM: Homo sapiens
<220> FEATURE:
<221> NAME/KEY: DISULFID
<222> LOCATION: (7)..(7)
<223> OTHER INFORMATION: Interchain disulphide bond between Cys7 of SEQ
      ID NO: 1 and Cys7 of SEQ ID NO: 2
<220> FEATURE:
<221> NAME/KEY: DISULFID
<222> LOCATION: (20)..(20)
<223> OTHER INFORMATION: Interchain disulphide bond between Cys20 of SEQ
      ID NO: 1 and Cys19 of SEQ ID NO: 2

<400> SEQUENCE: 1

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 2
<211> LENGTH: 30
<212> TYPE: PRT
<213> ORGANISM: Homo sapiens
<220> FEATURE:
<221> NAME/KEY: DISULFID
<222> LOCATION: (7)..(7)
<223> OTHER INFORMATION: Interchain disulphide bond between Cys7 of SEQ
      ID NO: 1 and Cys7 of SEQ ID NO: 2
<220> FEATURE:
<221> NAME/KEY: DISULFID
<222> LOCATION: (19)..(19)
<223> OTHER INFORMATION: Interchain disulphide bond between Cys20 of SEQ
      ID NO: 1 and Cys19 of SEQ ID NO: 2

<400> SEQUENCE: 2

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30
```

```
<210> SEQ ID NO 3
<211> LENGTH: 30
<212> TYPE: PRT
<213> ORGANISM: Artificial sequence
<220> FEATURE:
<223> OTHER INFORMATION: Synthetic sequence: Insulin lispro, a
      fast-acting insulin analogue

<400> SEQUENCE: 3

Phe Val Asn Gln His Leu Cys Gly Ser His Leu Val Glu Ala Leu Tyr
1               5                   10                  15

Leu Val Cys Gly Glu Arg Gly Phe Phe Tyr Thr Lys Pro Thr
            20                  25                  30

<210> SEQ ID NO 4
<211> LENGTH: 30
<212> TYPE: PRT
<213> ORGANISM: Artificial sequence
<220> FEATURE:
<223> OTHER INFORMATION: Synthetic sequence: Insulin aspart, a
      fast-acting insulin analogue

<400> SEQUENCE: 4

Phe Val Asn Gln His Leu Cys Gly Ser His Leu Val Glu Ala Leu Tyr
1               5                   10                  15

Leu Val Cys Gly Glu Arg Gly Phe Phe Tyr Thr Asp Lys Thr
            20                  25                  30

<210> SEQ ID NO 5
<211> LENGTH: 30
<212> TYPE: PRT
<213> ORGANISM: Artificial sequence
<220> FEATURE:
<223> OTHER INFORMATION: Synthetic sequence: Insulin glulisine, a
      fast-acting insulin analogue

<400> SEQUENCE: 5

Phe Val Lys Gln His Leu Cys Gly Ser His Leu Val Glu Ala Leu Tyr
1               5                   10                  15

Leu Val Cys Gly Glu Arg Gly Phe Phe Tyr Thr Pro Glu Thr
            20                  25                  30
```